US012623012B2

(12) United States Patent
Pitchaimani et al.

(10) Patent No.: US 12,623,012 B2
(45) Date of Patent: May 12, 2026

(54) PERITONEAL DIALYSIS SYSTEM INCLUDING PERISTALTIC PUMP

(71) Applicants: VANTIVE US HEALTHCARE LLC, Deerfield, IL (US); VANTIVE HEALTH GMBH, Glattpark (CH)

(72) Inventors: Karthik Pitchaimani, Bangalore (IN); Anoop Ta, Kerla (IN); Sadashiva Kamath, Bengaluru (IN); Akhilesh Sv, Bangalore (IN)

(73) Assignees: Vantive US Healthcare LLC, Deerfield, IL (US); Vantive Health GMBH, Glattpark (CH)

( * ) Notice: Subject to any disclaimer, the term of this patent is extended or adjusted under 35 U.S.C. 154(b) by 411 days.

(21) Appl. No.: 18/269,590

(22) PCT Filed: Dec. 7, 2021

(86) PCT No.: PCT/US2021/062199
§ 371 (c)(1),
(2) Date: Jun. 26, 2023

(87) PCT Pub. No.: WO2022/140054
PCT Pub. Date: Jun. 30, 2022

(65) Prior Publication Data
US 2024/0058515 A1 Feb. 22, 2024

(30) Foreign Application Priority Data
Dec. 24, 2020 (IN) .............................. 202041056330

(51) Int. Cl.
| | |
|---|---|
| *A61M 1/28* | (2006.01) |
| *A61M 1/14* | (2006.01) |
| *A61M 1/16* | (2006.01) |

(52) U.S. Cl.
CPC .......... *A61M 1/281* (2014.02); *A61M 1/1524* (2022.05); *A61M 1/154* (2022.05);
(Continued)

(58) Field of Classification Search
CPC .... A61M 1/1524; A61M 1/154; A61M 1/155; A61M 1/1565; A61M 1/159;
(Continued)

(56) References Cited

U.S. PATENT DOCUMENTS

| | | |
|---|---|---|
| 2005/0209563 A1 | 9/2005 | Hopping et al. |
| 2016/0106904 A1 | 4/2016 | Cicchello et al. |

FOREIGN PATENT DOCUMENTS

| | | |
|---|---|---|
| EP | 3 222 305 | 1/2019 |

OTHER PUBLICATIONS

International Search Report for PCT/US2021/062199 dated Dec. 7, 2021—5 pages.
(Continued)

*Primary Examiner* — John Kim
(74) *Attorney, Agent, or Firm* — K&L Gates LLP

(57) ABSTRACT

A peritoneal dialysis ("PD") system includes a cycler having a peristaltic pump actuator; a disposable set including a pressure sensing manifold including first and second pressure sensing pods, a drain line and a first dialysis fluid/heater container line in fluid communication with the first pressure sensing pod, and at least one dialysis fluid container line and a patient line in fluid communication with the second pressure sensing pod; and a control unit programmed to operate the peristaltic pump actuator (i) in a first direction to pump fresh dialysis fluid along the at least one additional dialysis fluid container line into the first dialysis fluid/heater line and (ii) in a second direction to pump heated fresh dialysis fluid along the first dialysis fluid/heater line into the patient line. The pump actuator may be operated in the first
(Continued)

direction again to pump used dialysis fluid from the patient
to a drain.

25 Claims, 16 Drawing Sheets

(52) U.S. Cl.
CPC .......... *A61M 1/155* (2022.05); *A61M 1/1565*
(2022.05); *A61M 1/159* (2022.05); *A61M
1/1629* (2014.02); *A61M 1/282* (2014.02);
*A61M 2205/12* (2013.01); *A61M 2205/128*
(2013.01); *A61M 2205/3331* (2013.01); *A61M
2205/3337* (2013.01); *A61M 2205/3341*
(2013.01); *A61M 2205/3365* (2013.01)
(58) Field of Classification Search
CPC .... A61M 1/1629; A61M 1/281; A61M 1/282;
A61M 2205/12; A61M 2205/128; A61M
2205/3331; A61M 2205/3337; A61M
2205/3341; A61M 2205/3365
See application file for complete search history.

(56) References Cited

OTHER PUBLICATIONS

Written Opinion for PCT/US2021/062199 dated Dec. 7, 2021.
IPRP for PCT/US2021/062199 dated Mar. 17, 2023.

PERITONEAL DIALYSIS SYSTEM INCLUDING PERISTALTIC PUMP

PRIORITY CLAIM

The present application is a national phase entry of PCT Patent Application No. PCT/US2021/062199, filed on Dec. 7, 2021, which claims priority to and the benefit of Indian Patent Application number 202041056330, filed on Dec. 24, 2020, the entirety of which are herein incorporated by reference.

TECHNICAL FIELD

The present disclosure relates generally to medical fluid treatments and in particular to dialysis fluid treatments.

BACKGROUND

Due to various causes, a person's renal system can fail. Renal failure produces several physiological derangements. It is no longer possible to balance water and minerals or to excrete daily metabolic load. Toxic end products of metabolism, such as, urea, creatinine, uric acid and others, may accumulate in a patient's blood and tissue.

Reduced kidney function and, above all, kidney failure is treated with dialysis. Dialysis removes waste, toxins and excess water from the body that normal functioning kidneys would otherwise remove. Dialysis treatment for replacement of kidney functions is critical to many people because the treatment is lifesaving.

One type of kidney failure therapy is Hemodialysis ("HD"), which in general uses diffusion to remove waste products from a patient's blood. A diffusive gradient occurs across the semi-permeable dialyzer between the blood and an electrolyte solution called dialysate or dialysis fluid to cause diffusion.

Hemofiltration ("HF") is an alternative renal replacement therapy that relies on a convective transport of toxins from the patient's blood. HF is accomplished by adding substitution or replacement fluid to the extracorporeal circuit during treatment. The substitution fluid and the fluid accumulated by the patient in between treatments is ultrafiltered over the course of the HF treatment, providing a convective transport mechanism that is particularly beneficial in removing middle and large molecules.

Hemodiafiltration ("HDF") is a treatment modality that combines convective and diffusive clearances. HDF uses dialysis fluid flowing through a dialyzer, similar to standard hemodialysis, to provide diffusive clearance. In addition, substitution solution is provided directly to the extracorporeal circuit, providing convective clearance.

Most HD, HF, and HDF treatments occur in centers. A trend towards home hemodialysis ("HHD") exists today in part because HHD can be performed daily, offering therapeutic benefits over in-center hemodialysis treatments, which occur typically bi- or tri-weekly. Studies have shown that more frequent treatments remove more toxins and waste products and render less interdialytic fluid overload than a patient receiving less frequent but perhaps longer treatments. A patient receiving more frequent treatments does not experience as much of a down cycle (swings in fluids and toxins) as does an in-center patient, who has built-up two or three days' worth of toxins prior to a treatment. In certain areas, the closest dialysis center can be many miles from the patient's home, causing door-to-door treatment time to consume a large portion of the day. Treatments in centers close to the patient's home may also consume a large portion of the patient's day. HHD can take place overnight or during the day while the patient relaxes, works or is otherwise productive.

Another type of kidney failure therapy is peritoneal dialysis ("PD"), which infuses a dialysis solution, also called dialysis fluid, into a patient's peritoneal chamber via a catheter. The dialysis fluid is in contact with the peritoneal membrane in the patient's peritoneal chamber. Waste, toxins and excess water pass from the patient's bloodstream, through the capillaries in the peritoneal membrane, and into the dialysis fluid due to diffusion and osmosis, i.e., an osmotic gradient occurs across the membrane. An osmotic agent in the PD fluid provides the osmotic gradient. Used or spent dialysis fluid is drained from the patient, removing waste, toxins and excess water from the patient. This cycle is repeated, e.g., multiple times.

There are various types of peritoneal dialysis therapies, including continuous ambulatory peritoneal dialysis ("CAPD"), automated peritoneal dialysis ("APD"), tidal flow dialysis and continuous flow peritoneal dialysis ("CFPD"). CAPD is a manual dialysis treatment. Here, the patient manually connects an implanted catheter to a drain to allow used or spent dialysis fluid to drain from the peritoneal chamber. The patient then switches fluid communication so that the patient catheter communicates with a bag of fresh dialysis fluid to infuse the fresh dialysis fluid through the catheter and into the patient. The patient disconnects the catheter from the fresh dialysis fluid bag and allows the dialysis fluid to dwell within the peritoneal chamber, wherein the transfer of waste, toxins and excess water takes place. After a dwell period, the patient repeats the manual dialysis procedure, for example, four times per day. Manual peritoneal dialysis requires a significant amount of time and effort from the patient, leaving ample room for improvement.

Automated peritoneal dialysis ("APD") is similar to CAPD in that the dialysis treatment includes drain, fill and dwell cycles. APD machines, however, perform the cycles automatically, typically while the patient sleeps. APD machines free patients from having to manually perform the treatment cycles and from having to transport supplies during the day. APD machines connect fluidly to an implanted catheter, to a source or bag of fresh dialysis fluid and to a fluid drain. APD machines pump fresh dialysis fluid from a dialysis fluid source, through the catheter and into the patient's peritoneal chamber. APD machines also allow for the dialysis fluid to dwell within the chamber and for the transfer of waste, toxins and excess water to take place. The source may include multiple liters of dialysis fluid including several solution bags.

APD machines pump used or spent dialysate from the patient's peritoneal cavity, though the catheter, and to the drain. As with the manual process, several drain, fill and dwell cycles occur during dialysis. A "last fill" may occur at the end of the APD treatment. The last fill fluid may remain in the peritoneal chamber of the patient until the start of the next treatment, or may be manually emptied at some point during the day.

Known APD systems include a machine or cycler that accepts and actuates a pumping cassette having a hard part and a soft part that is deformable for performing pumping and valving operations. Sealing the fluid disposable cassette with a pneumatic path via a gasket to provide actuation has proven to be a potential field issue, which can delay treatment start time and affect user experience. Pneumatic cassette systems also produce acoustic noise, which may be a source of customer dissatisfaction.

For each of the above reasons, an improved APD machine is needed.

SUMMARY

The present disclosure sets forth a streamlined automated peritoneal dialysis ("APD") cycler and associated system providing a peristaltic pump and disposable set that organizes tubing and performs many functions discussed below. The cycler of the system in one embodiment includes a peristaltic pump actuator that is capable of pumping in two directions. Flow in either direction advances through a pressure sensing manifold, which is part of an overall disposable set, and which may be separated into two pressure sensing pods, a first pressure sensing pod and a second pressure sensing pod. Both pressure sensing pods include a pressure sensing diaphragm that separates a liquid side for receiving dialysis fluid (fresh unheated dialysis fluid, fresh heated dialysis fluid and used dialysis fluid) from a pressure transmission side that holds a transmission fluid (e.g., air) for transmitting fluid pressure to a pressure transducer. The pressure sensing pods sense both positive and negative fluid pressure and output pressure signals to a control unit that uses a control algorithm configured to control the speed of a peristaltic pump actuator to ensure that the pumping pressure to the patient is within a safe limit, e.g., +1.5 psig to +9 psig for positive pressure pumping to the patient and −1.0 psig to −3 psig for negative pressure pumping from the patient. Pumping to and from the heater container or to drain may be performed at higher pressures if desired. The pumping pressures are controlled in an embodiment using feedback from the pod pressure sensors in an algorithm, e.g., using proportional, integral and derivative ("PID") routine, which determines how much current to deliver to the peristaltic pump actuator. The pressure readings from the pressure pods may be used as feedback (i) continuously over the entire course of a patient fill or drain, (ii) only at critical times such as the beginning and end of a fill or drain, (iii) or at such critical times in combination with intermittent or periodic pressure checks during a middle portion of a fill or drain.

In one embodiment, the first pressure sensing pod operates with a drain line and a first dialysis fluid/heater container line, while the second pressure sensing pod operates with a patient line and second and third additional dialysis fluid lines. The drain line may run to a house drain (toilet, bathtub or sink) or to a drain container. The first dialysis fluid container is placed atop a batch heater of the cycler, e.g., a resistive plate heater, for a first patient fill. After the first dialysis fluid from the first container is heated and delivered to the patient, fresh dialysis fluid is pulled from a second or third dialysis fluid container and is delivered to the first dialysis fluid container for heating (e.g., while the first solution fluid dwells within the patient).

In an alternative embodiment, the batch heater is replaced with an inline heater provided by the cycler, which heats fresh dialysis fluid as it flows through the patient line to the patient. The batch and inline dialysis fluid heaters both operate with one or more temperature sensor to sense the temperature of the heated, fresh dialysis fluid to use as feedback to the control unit for controlling the heater, e.g., via a PID algorithm.

Each of the fluid lines mentioned above may be placed in a pinch valve provided by the cycler, which are each under selective control of the control unit in one embodiment. The pinch valves may be electrically actuated solenoid valves that energize open for fail safe operation. In an alternative embodiment, the pinch valves are replaced by multiway valves, e.g., stopcock valves, which operate with the pressure sensing manifold and the fluid lines. The multiway valves selectively allow flow into and out of desired ports of the pressure sensing pods. It should be appreciated that in certain instances, the rollers of the peristaltic pump actuator may also be used as an occluder or valve, which may reduce the number of valves needed and act as a backup in case of a valve malfunction.

Regardless of the type of valves, the control of the valves in combination with the direction of the peristaltic pump actuator dictates the direction of fluid flow. Different fluid paths include (i) from the first dialysis fluid/heater container to the patient, (ii) from either of the second or third dialysis fluid containers to the first dialysis fluid/heater container, and (iii) from the patient to drain, e.g., house drain or drain container.

Combinations of fluid paths (i) to (iii), or portions thereof, are used for priming the disposable set prior to treatment. One or more priming or air sensor may be provided by the cycler, e.g., an optical or capacitance sensor, for detecting the presence of liquid. The one or more priming or air sensor is located so as to operate with (i) the patient line (to determine when the patient line is fully primed prior to connection with the patient's catheter and to look for air during treatment) and (ii) the heating line (e.g., to look for air during treatment that may come out of solution due to fluid heating).

The cycler may further provide a flow sensor that invasively or non-invasively measure flowrate, e.g., along the patient line. The control unit of the cycler may integrate the measured flowrate to determine a volume of fresh dialysis fluid delivered to the patient and a volume of used dialysis fluid removed from the patient. The control unit also determines the difference between those values to arrive at an amount of ultrafiltration ("UF") removed from the patient. In an alternative embodiment, a weigh scale provided with the dialysis fluid heater may be used to weigh fresh dialysis fluid delivered to the patient and used dialysis fluid removed from the patient. A single weigh scale may be used with the heating container for fresh dialysis fluid and the drain container for used dialysis fluid. Alternatively, separate dedicated fresh dialysis fluid and used dialysis fluid scales may be provided.

In one embodiment, the control unit includes one or more processor, one or more memory and a video controller operating with a user interface provided to control each of the peristaltic pump actuator, the dialysis fluid valves and the heater, and to receive signals from each of the pressure sensing pods, the priming or air sensor, the flow or weight sensors if provided, and one or more temperature sensor associated with the batch or inline heater. The user interface may be provided with a touchscreen and/or electromechanical pushbuttons to allow the user or patient to enter parameters for treatment and a display screen for providing information, such as treatment status information.

The control unit may also be programmed to monitor for a patient empty detection based on a pressure monitoring algorithm using measurements taken at the pressure sensing manifold. A characteristic increase in negative or suction pressure in the patient line at the end of a patient drain as measured by at least one of the pressure sensing pods indicates a patient empty condition to the control unit. A fluid pushback within the patient line may be employed as part of the patient empty algorithm. The patient empty detection is believed to be relatively quick, which reduces the amount of time that the patient is subjected to increased negative patient pressures.

The control unit of the cycler may also detect a patient line occlusion based on a pressure rise or decay algorithm. Again, a characteristic increase in suction or negative pressure in the patient line measured by at least one of the pressure sensing pods during a patient drain indicates an occlusion to the control unit, while a rise in positive pressure in the patient line measured by at least one of the pressure sensing pods during a patient fill indicates an occlusion to the control unit. Fluid pushback attempts within the patient line may again be employed as a result of the occlusion algorithms.

It is contemplated that the peristaltic pumping system of the present disclosure allows for a partial or perhaps even a full PD fluid flowrate to be maintained even during partial negative and positive occlusions. In this manner, treatment times may be maintained or almost maintained even when an occlusion is present. Thus, the usual response to an occlusion, namely to stop treatment, wake the patient, and instruct the patient to clear the occlusion if possible, is not necessarily the response with the system of the present disclosure. If, for example, the drain or fill is almost complete, the system of the present disclosure may determine that it is best to complete the fill or drain at the present flowrate and then try to clear the occlusion once the drain or fill is completed.

The control unit may further additionally be programmed to perform a patient fill according to a fill profile in which a speed of the peristaltic pump actuator operating in the second direction is increased during a middle portion of the patient fill. The control unit may still further additionally be programmed to perform a patient drain according to a drain profile in which a speed of the peristaltic pump actuator operating in the first direction is increased during a middle portion of the patient drain. In any case, the peristaltic pumping system of the present disclosure provides a wide range of flowrates, e.g. from less than ten mL/min to greater than 350 mL/min, while ensuring that positive or negative patient pressures are maintained within limits. The peristaltic pumping is also relatively smooth, allowing for minimal flow pulsation across treatment.

The pressure sensing manifold, the fluid lines and fluid containers of the disposable set may be made of one or more plastic, e.g., polyvinylchloride ("PVC") or a non-PVC material, such as polyethylene ("PE"), polyurethane ("PU") or polycarbonate ("PC"). The housing of the cycler may be made of any of the above plastics, and/or of metal, e.g., stainless steel, steel and/or aluminum.

In light of the disclosure set forth herein, and without limiting the disclosure in any way, in a first aspect, which may be combined with any other aspect described herein, or portion thereof, a peritoneal dialysis system includes (i) a cycler having a peristaltic pump actuator; a disposable set including a pressure sensing manifold including first and second pressure sensing pods, a drain line and a first dialysis fluid/heater container line in fluid communication with the first pressure sensing pod, and at least one additional dialysis fluid container line and a patient line in fluid communication with the second pressure sensing pod; and a control unit programmed to operate the peristaltic pump actuator (i) in a first direction to pump fresh dialysis fluid along the at least one additional dialysis fluid container line into the first dialysis fluid/heater line and (ii) in a second direction to pump heated, fresh dialysis fluid along the first dialysis fluid/heater line into the patient line.

In a first aspect, which may be combined with any other aspect described herein, or portion thereof, the peritoneal dialysis system includes a peristaltic pumping tube in fluid communication with the first and second pressure sensing pods.

In a third aspect, which may be combined with any other aspect described herein, or portion thereof, at least one of the drain line or the first dialysis fluid/heater container line is connected to a port extending from the first pressure sensing pod.

In a fourth aspect, which may be combined with any other aspect described herein, or portion thereof, at least one of the at least one additional dialysis fluid container line or the patient line is connected to a port extending from the second pressure sensing pod.

In a fifth aspect, which may be combined with any other aspect described herein, or portion thereof, the control unit is configured to use an output from the first pressure sensing pod as feedback to control pumping in the first direction at or below a positive system pressure limit for moving fresh dialysis fluid to a dialysis fluid/heater container.

In a sixth aspect, which may be combined with any other aspect described herein, or portion thereof, the control unit is configured to use an output from the second pressure sensing pod as feedback to control pumping in the first direction at or below a negative system pressure limit for moving fresh dialysis fluid to a dialysis fluid/heater container.

In a seventh aspect, which may be combined with any other aspect described herein, or portion thereof, the control unit is configured to use an output from the second pressure sensing pod as feedback to control pumping in the second direction at or below a positive patient pressure limit for moving fresh dialysis fluid to a patient.

In an eighth aspect, which may be combined with any other aspect described herein, or portion thereof, the control unit is configured to use an output from the second pressure sensing pod as feedback to control pumping in the first direction at or below a negative patient pressure limit for removing used dialysis fluid from a patient.

In a ninth aspect, which may be combined with any other aspect described herein, or portion thereof, the cycler further includes at least one of a drain valve for operating with the drain line, a dialysis fluid/heater valve for operating with the first dialysis fluid/heater container line, at least one additional dialysis fluid container valve for operating with the at least one additional dialysis fluid container line, or a patient valve for operating with the patient line.

In a tenth aspect, which may be combined with any other aspect described herein, or portion thereof, the cycler further includes at least one of a first multiway valve actuator for operating with the first pressure sensing pod to allow flow to either the drain line or the first dialysis fluid/heater container line, or a second multiway valve actuator for operating with the second pressure sensing pod to allow flow to either the patient line or one of the at least one additional dialysis fluid container line.

In an eleventh aspect, which may be combined with any other aspect described herein, or portion thereof, the cycler further includes a heater under control of the control unit for heating fresh dialysis fluid delivered to a first dialysis fluid/heater container via the first dialysis fluid/heater container line.

In a twelfth aspect, which may be combined with any other aspect described herein, or portion thereof, at least one of the first and second pressure sensing pods includes a flexible diaphragm that transmits fresh and used dialysis fluid pressure fluctuations to a pressure transmission fluid.

In a thirteenth aspect, which may be combined with any other aspect described herein, or portion thereof, the flexible diaphragm is further configured to dampen pressure fluctuations.

In a fourteenth aspect, which may be combined with any other aspect described herein, or portion thereof, the control unit is further configured to end a patient drain when a negative pressure increase is sensed by the second pressure sensing pod while the peristaltic pump actuator is operated in the first direction to pump used dialysis fluid from the patient line.

In a fifteenth aspect, which may be combined with any other aspect described herein, or portion thereof, the control unit is configured to end the patient drain when the negative pressure increase is sensed and the control unit has determined that at least a threshold amount of used dialysis fluid has been removed from the patient.

In a sixteenth aspect, which may be combined with any other aspect described herein, or portion thereof, the control unit is configured to end the patient drain when the negative pressure increase is sensed and after a pushback of used dialysis fluid in the patient line by the peristaltic pump actuator operating in the second direction fails to remove the negative pressure increase.

In a seventeenth aspect, which may be combined with any other aspect described herein, or portion thereof, the control unit is further configured to determine that a patient line occlusion has occurred when the second pressure sensing pod senses an increase in positive pressure in the patient line while moving fresh dialysis fluid to a patient.

In an eighteenth aspect, which may be combined with any other aspect described herein, or portion thereof, the control unit is further configured to determine that a patient line occlusion has occurred when the second pressure sensing pod senses an increase in negative pressure in the patient line while removing used dialysis fluid from a patient.

In a nineteenth aspect, which may be combined with any other aspect described herein, or portion thereof, the control unit is further configured to perform a patient fill according to a fill profile in which a speed of the peristaltic pump actuator operating in the second direction is increased for a middle portion of the patient fill.

In a twentieth aspect, which may be combined with any other aspect described herein, or portion thereof, the control unit is further configured to perform a patient drain according to a drain profile in which a speed of the peristaltic pump actuator operating in the first direction is increased for a middle portion of the patient drain.

In a twenty-first aspect, which may be combined with any other aspect described herein, or portion thereof, the peristaltic pump actuator is positioned relative to the cycler such that the first and second pressure sensing pods, the drain line, the first dialysis fluid/heater container line, the at least one additional dialysis fluid container line and the patient are oriented at least substantially horizontally for treatment.

In a twenty-second aspect, which may be combined with any other aspect described herein, or portion thereof, the peristaltic pump actuator is located on a tray that slides into and out of the cycler.

In a twenty-third aspect, which may be combined with any other aspect described herein, or portion thereof, the peristaltic pump actuator is accessible from a top of the cycler.

In a twenty-fourth aspect, which may be combined with any other aspect described herein, or portion thereof, the peristaltic pump actuator is positioned relative to the cycler such that the first and second pressure sensing pods, the drain line, the first dialysis fluid/heater container line, the at least one additional dialysis fluid container line and the patient are oriented at least substantially vertically for treatment.

In a twenty-fifth aspect, which may be combined with any other aspect described herein, or portion thereof, the cycler further includes a plurality of valves, a first door configured to selectively cover the plurality of valves and a second door configured to selectively cover the peristaltic pump actuator.

In a twenty-sixth aspect, which may be combined with any other aspect described herein, or portion thereof, the first and second pressure sensing pods are spaced at least one of (i) symmetrically about or (ii) equidistant to the peristaltic pump actuator.

In a twenty-seventh aspect, which may be combined with any other aspect described herein, or portion thereof, a peritoneal dialysis system includes a first peristaltic pump actuator; a second peristaltic pump actuator; a disposable set including a first peristaltic pumping tube operable with the first peristaltic pump actuator, the first peristaltic pumping tube outputting to a second peristaltic pumping tube operable with the second peristaltic pump actuator; and a control unit programmed to operate a first speed of the first peristaltic pump actuator as a function of a second speed of the second peristaltic pump actuator.

In a twenty-eighth aspect, which may be combined with any other aspect described herein, or portion thereof, the function is constant or periodic.

In a twenty-ninth aspect, which may be combined with any other aspect described herein, or portion thereof, the control unit is programmed to operate the second speed based on a set dialysis fluid flowrate.

In a thirtieth aspect, which may be combined with any other aspect described herein, or portion thereof, the control unit is programmed to operate the first peristaltic pump actuator so as to create a desired inlet pressure to the second peristaltic pumping tube.

In a thirty-first aspect, any of the features, functionality and alternatives described in connection with any one or more of FIGS. 1 to 17 may be combined with any of the features, functionality and alternatives described in connection with any other of FIGS. 1 to 17.

It is accordingly an advantage of the present disclosure to provide an APD system having a peristaltic pump and valves that collectively reduce operating noise and which maintain and improve treatment time due to range of peristaltic pump ability.

It is another advantage of the present disclosure to provide an APD system that is portable to ultra-portable.

It is a further advantage of the present disclosure to provide an APD system that eliminates certain sealing issues present in known APD systems.

It is yet a further advantage of the present disclosure to provide an APD pump driven system that eliminates bulky pneumatic equipment associated with certain APD systems.

It is yet a further advantage of the present disclosure to provide an APD pump driven system that reduces noise relative to pneumatic systems.

It is yet another advantage of the present disclosure to provide an APD system that manages peritoneal dialysis fluid flow so as to be within safe and comfortable patient pressure limits.

Still another advantage of the present disclosure is to provide an APD system having improved empty detection, resulting in lower time of patient exposure to low pressure during empty detection.

Still a further advantage of the present disclosure is to provide an APD system having lessened flow pulsation for improved patient comfort.

Yet another advantage of the present disclosure is to provide an APD system that is suited for inline heating to further improve treatment time and reduce device size.

Yet a further advantage of the present disclosure is to provide an APD system having reduced disposable integrity test duration.

Additional features and advantages are described in, and will be apparent from, the following Detailed Description and the Figures. The features and advantages described herein are not all-inclusive and, in particular, many additional features and advantages will be apparent to one of ordinary skill in the art in view of the figures and description. Also, any particular embodiment does not have to have all of the advantages listed herein and it is expressly contemplated to claim individual advantageous embodiments separately. Moreover, it should be noted that the language used in the specification has been selected principally for readability and instructional purposes, and not to limit the scope of the inventive subject matter.

DETAILED DESCRIPTION

Figure 1:
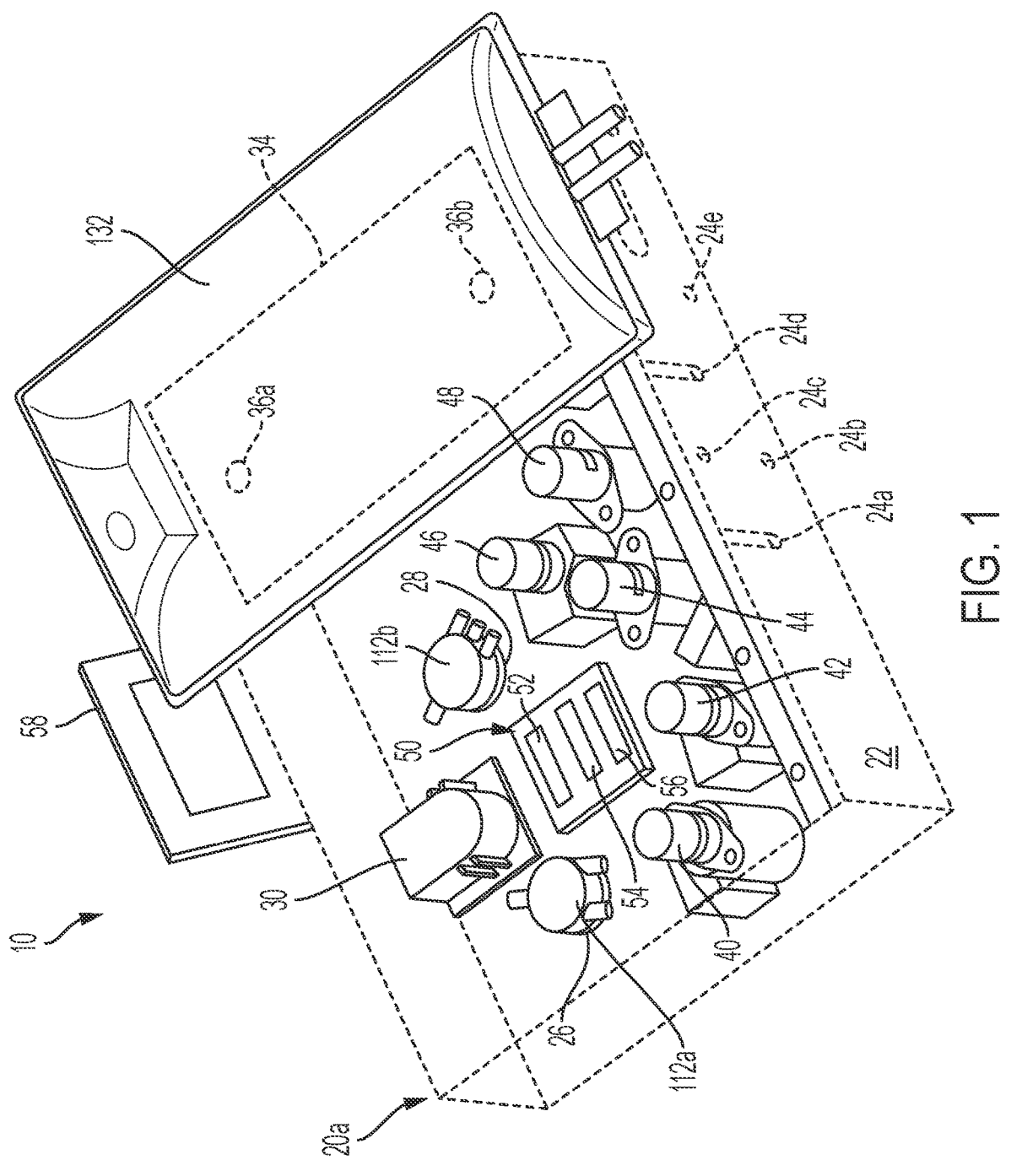
FIG. 1 is a perspective view of one embodiment of an automated peritoneal dialysis ("APD") cycler for the peristaltic pump-based system of the present disclosure.
Figure 2:
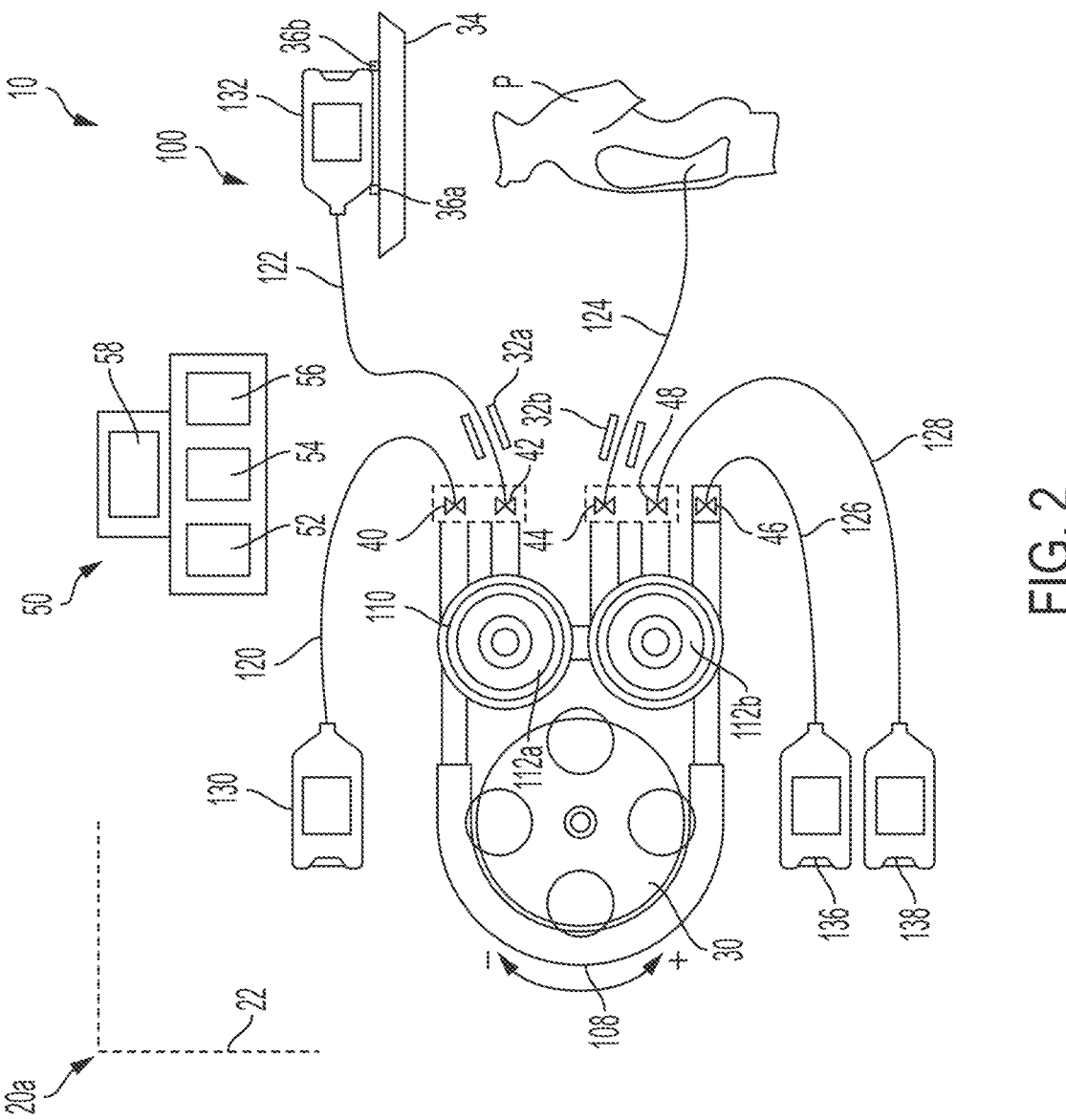
FIG. 2 is a schematic view of one embodiment for a flow arrangement for the peristaltic pump-based system of the present disclosure.
Figure 3:
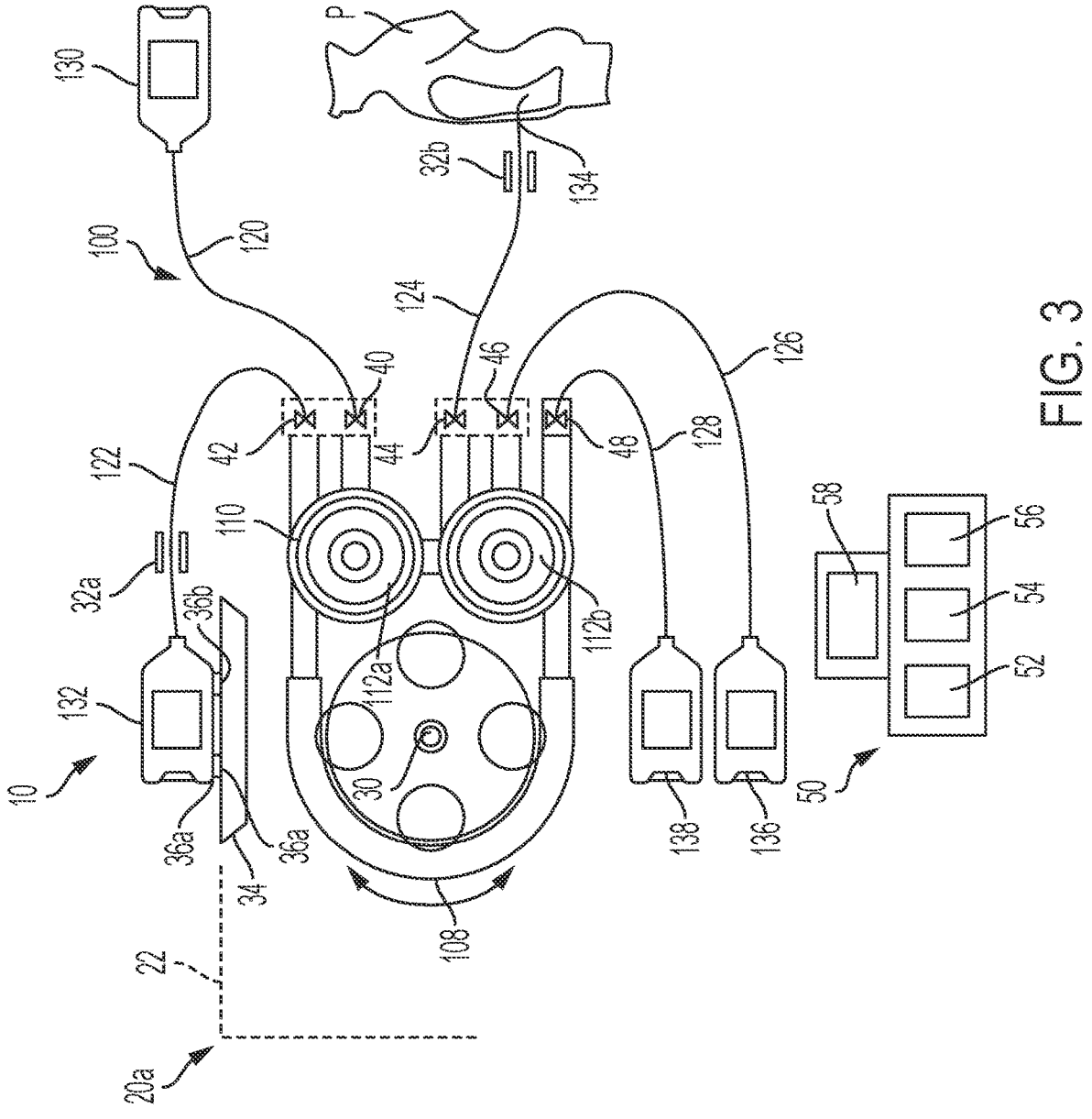
FIG. 3 is a schematic view of another embodiment for a flow arrangement for the peristaltic pump-based system of the present disclosure.

Referring now to the drawings and in particular to FIG. 1, an embodiment of system 10 includes an automated peritoneal dialysis ("APD") cycler 20a having a housing 22, which uses peristaltic pumping in the illustrated embodiment, and which operates a disposable set 100 (see FIGS. 2 and 3). All rigid and flexible tubing portions of disposable set 100 may be made of one or more plastic, e.g., polyvinylchloride ("PVC") or a non-PVC material, such as polyethylene ("PE"), polyurethane ("PU") or polycarbonate ("PC"). Housing 22 of cycler 20a may be made of any of the above plastics, and/or of metal, e.g., stainless steel, steel and/or aluminum.

Housing 22 is shown in phantom line to see the components of system 10 provided inside. In the illustrated embodiment, housing 22 is provided with a series of holes or slots 24a, 24b, 24c, 24d and 24e for tubing of disposable set 100 to extend from the inside of housing 22 to the outside of the housing. While illustrated as round holes, the apertures may alternatively be slots that 24a, 24b, 24c, 24d and 24e that extend up along a front surface of housing 22 (see e.g., slots 24a and 24c), through an upper edge of the front surface, so that with the lid of cycler 20a lifted, the patient or caregiver may translatingly insert the tubes of disposable set 100 down into the slots, and wherein various tubes may be preconnected to the dialysis fluid containers or bags and possibly a drain container or bag.

FIG. 1 also illustrates that housing 22 of cycler 20a of system 10 houses a peristaltic pump actuator 30, which is variable speed and rotates in two directions in one embodiment. The peristaltic pumping tube operating with peristaltic pump actuator 30 extends to two pressure sensing pods 112a and 112b, which operate respectively with reusable pressure transducers 26 and 28 located within housing 22. Multiple tubes extend from pressure sensing pods 112a and 112b and individually through pinch valves 40, 42, 44, 46 and 48 and from there through holes or slots 24a, 24b, 24c, 24d and 24e. Pinch valves 40, 42, 44, 46 and 48 in one embodiment are electrically actuated solenoid valves that energize open so as to operate in a fail safe manner. In an alternative embodiment discussed below, pinch valves 40, 42, 44, 46 and 48 are replaced with multiway stopcock valves that interface directly with pressure sensing pods 112a and 112b.

FIG. 1 further illustrates that housing 22 of cycler 20a of system 10 houses a heater 34, which in one embodiment is attached to and openable with the lid of housing 22. Heater 34 is in one embodiment a batch heater that heats an entire fill volume worth of fresh dialysis fluid, e.g., before treatment for a first patient fill and during a patient dwell for subsequent patient fills. One or more temperature sensor 36a and 36b is provided and located so as to measure the temperature of fresh dialysis fluid located within a container or bag placed on top of heater 34. The output of one or more temperature sensor 36a or 36b is used in an embodiment as feedback, e.g., via a proportional, integral, derivative ("PID") control routine, to control the power supplied to heater 34 in an attempt to heat the fresh dialysis fluid to body temperature, e.g., 37° C. Heater 34 in an alternative embodiment is an inline heater that heats the dialysis fluid flowing through a patient line or tube to the patient to body temperature.

Besides pressure transducers 26 and 28 and temperature sensors 36a and 36b, system 10 includes additional sensors discussed below. Each of the sensors of cycler 20a of system 10 discussed herein outputs in one embodiment to a control unit 50 illustrated in FIG. 1, which in addition controls the operation of peristaltic pump actuator 30, batch heater 34 (or alternatively an inline heater), and pinch valves 40, 42, 44, 46 and 48 (or alternatively the stopcock valves). Control unit 50 includes one or more processor 52, one or more memory 54 and a video controller 56 that controls a user interface 58, such as a touch screen user interface. User interface 58 may alternatively or additionally be a remote user interface, e.g., via a tablet or smartphone. Control unit 50 receives signals from pressure transducers 26 and 28 and uses the signals, e.g., via a PID control routine to control patient pumping pressure and other pumping pressures discussed herein via the control of current to peristaltic pump actuator 30. Pressure readings from the pressure pod transducers 26 and 28 may be used as feedback to control unit 50 (i) continuously over the entire course of a patient fill or drain, (ii) only at critical times such as the beginning and end of a fill or drain, (iii) or at such critical times in combination with intermittent or periodic pressure checks during a middle portion of a fill or drain. In an example, if a pressure signal received at control unit 50 exceeds a certain value (positive or negative), depending on the condition of a partial occlusion, control unit 50 may be configured to lower the speed of peristaltic pump actuator 30 to a specified level, which may be a single level or multiple, e.g., two, levels. Such a pumping regime ensures that the control of peristaltic pump actuator 30 is not complex and is achievable.

Control unit 50 may also include a transceiver and a wired or wireless connection to a network (not illustrated), e.g., the internet, for sending treatment data to and receiving prescription instructions/changes from a doctor's or clinician's server interfacing with a doctor's or clinician's computer. The data sent to the doctor's or clinician's computer may be analyzed and/or converted to, or used to form, other data useful for analysis. Such data conversion is performed alternatively at control unit 50.

FIGS. 2 and 3 each illustrate system 10 and are very similar, including the same components, which are numbered the same. FIGS. 2 and 3 illustrate peristaltic pump actuator 30, batch heater 34, temperature sensors 36a and 36b, and pinch valves 40, 42, 44, 46 and 48 discussed above with FIG. 1, each operating with control unit 50. Pressure sensing pods 112a and 112b discussed in FIG. 1 are also illustrated in FIG. 3. In the illustrated embodiment, pressure sensing pods 112a and 112b are provided as part of a single, e.g., rigid manifold 110, which in turn is provided as part of an overall disposable set 100. Disposable set 100 also includes a peristaltic pumping tube 108, which is actuated by peristaltic pump actuator 30 and is connected at either end to pressure sensing pods 112a and 112b of rigid manifold 110. In an embodiment, peristaltic pumping tube 108 has a shore hardness of at least 77A and perhaps much higher and is formed of a mix of polymer resin molecular weight and plasticizer selected to provide desired springback properties. A higher shore hardness value and desired polymer mix enable the peristaltic pumping tube to spring open to its original shape more accurately and for a longer period of time during pumping. Peristaltic pump actuator 30 likewise has sufficient stiffness to operate the stiffer pumping tube.

System 10 employs additional measures to increase the accuracy of the peristaltic pumping provided by actuator 30 and peristaltic pumping tube 108. For example, it is contemplated to increase the number of rollers of actuator 30, e.g., from three to five or six, to reduce flow pulsatility. As discussed herein, pressure sensing pods 112a and 112b also dampen pulsatility and provide uniform boundary conditions, which enables the pump behavior to be systematic and have less asymmetry. Pressure sensing pods 112a and 112b in one embodiment are symmetrically located in an equidistant manner about peristaltic pump actuator 30, further reducing asymmetry and its deviation. It is also contemplated for control unit 50 to operate peristaltic pump actuator 30 so that fluid resistance on a suction side of pump actuator 30 and pumping tube 108 during patient fills and drains is the same, providing hydraulic balancing that further reduces asymmetry.

Disposable set 100 further includes a drain line or tube 120, a first fresh dialysis fluid/heating container or bag line or tube 122, a patient line or tube 124, a second dialysis fluid container or bag line or tube 126 and a third dialysis fluid container or bag line or tube 128, which may be a last fill container or bag.

The primary difference between FIGS. 2 and 3 is the order in which the different lines or tubes extend from rigid manifold 110. In FIGS. 2 and 3, patient line or tube 124 is located in the same position relative to rigid manifold 110. But in FIG. 2, drain line or tube 120 is located on top, while first fresh dialysis fluid/heating container or bag line or tube 122 is located beneath drain line 120. In FIG. 3, first fresh dialysis fluid/heating container or bag line or tube 122 is located on top, while drain line or tube 120 is located beneath the bag/heating line 122. Also, in FIG. 2, third dialysis fluid container or bag line 128 is located above second dialysis fluid container or bag line 126, while in FIG. 3, second dialysis fluid container or bag line 126 is located above third dialysis fluid container or bag line 128. FIGS. 2 and 3 illustrate that different lines or tubes may be located in different orientations. Also, FIG. 1 illustrates that rigid manifold 110, pressure sensing pods 112a and 112b and associated tubes 108, 120, 122, 124, 126 and 128 may be oriented horizontally during operation, while FIGS. 2 and 3 illustrate that rigid manifold 110, pressure sensing pods 112a and 112b and associated tubes 108, 120, 122, 124, 126 and 128 are oriented vertically during operation.

In general, if disposable set 100 is door loading, such that it is mounted vertically on the cycler, it is desirable to position drain line 120 on top for better air management. If disposable set 100 is instead top loading, such that it is mounted horizontally onto the cycler, the positions of drain line 120 and dialysis fluid/heating line 122 are interchangeable. The positions of second dialysis fluid line 126 versus third dialysis fluid (last bag) line 128 are also generally interchangeable. Patient line 124 and third dialysis fluid line 128 (in FIG. 2) or patient line 124 and second dialysis fluid line 126 (in FIG. 3) are positioned next to each other so that a single multiway or "3 by 2" pinch valve may be provided to control both lines, reducing the number of valve motors if motorized valves are employed. Patient line 124 may be provided above or below third dialysis fluid line 128 (in FIG. 2) or above or below second dialysis fluid line 126 (in FIG. 3).

In FIG. 3 for example, with a reduced number of valves using a "3 by 2" valve, either patient line 124 or second dialysis fluid line 126 bag will be open, while third dialysis fluid line 128 (e.g., for a last fill of fluid different from that in second dialysis fluid line 126) has independent control. For example, during a patient fill using open patient line 124, second and third dialysis fluid lines 126 and 128 are closed. During a heater bag replenish using open second dialysis fluid line 126, patient line 124 and third dialysis fluid line 128 are closed.

Providing independent valves instead allows the ordering of patient line 124, second dialysis fluid line 126 and third dialysis fluid line 128 to be completely flexible. The APD systems for cyclers 20a to 20f are configurable to have many different valve options, for example, (i) two "3 by 2" pinch valves and a single pinch valve (three motors), (ii) five pinch valves (five motors but independent line control), (iii) stopcock valves (two motors and independent line control) or (iv) combinations thereof.

Regardless of the orientation of rigid manifold 110, pressure sensing pods 112a and 112b and associated tubes, and regardless of the relative position of drain line 120 versus first dialysis fluid/heating line 122 and the relative position of second dialysis fluid line 126 versus third dialysis fluid line 128, it is contemplated that the fluid lines be positioned according to the following guidelines. First, patient line or tube 124 needs to be located on the other side of peristaltic pump actuator 30 from drain line or tube 120, so that peristaltic pump actuator 30 in FIGS. 2 and 3 may be rotated in the clockwise direction to remove effluent from patient P to the drain. Second, first fresh dialysis fluid/heating container or bag line or tube 122 needs to be located on the other side of peristaltic pump actuator 30 from second and third dialysis fluid lines or tubes 126 and 128, so that peristaltic pump actuator 30 in FIGS. 2 and 3 may be rotated again in the clockwise direction to pump fresh dialysis fluid along second and third dialysis fluid lines or tubes 126 and 128 into first fresh dialysis fluid/heating container or bag line or tube 122 in subsequent fills for heating. Third, first fresh dialysis fluid/heating container or bag line or tube 122 needs to be located on the other side of peristaltic pump actuator 30 from patient line or tube 124, so that peristaltic pump actuator 30 in FIGS. 2 and 3 may be rotated in the counterclockwise direction to pump heated, fresh dialysis fluid along first fresh dialysis fluid/heating container or bag line or tube 122 to patient P for filling. It should be appreciated that in FIGS. 2 and 3, especially in a top loading configuration, where air mitigation is not as much of a factor, the relative positions of lines 120 and 122 versus lines 124, 126 and 128 may be reversed, which would reverse the clockwise and counterclockwise directions just discussed.

FIG. 3 illustrates that disposable set 100 also includes a drain container or bag 130 connected to or in fluid communication with a distal end of drain line or tube 120. FIG. 2 illustrates instead that drain line or tube 120 may extend to a house drain, e.g., toilet, sink or bathtub. FIGS. 2 and 3 illustrate that disposable set 100 also includes a first fresh dialysis fluid/heating container or bag 132 connected to or in fluid communication with a distal end of first fresh dialysis fluid/heating container or bag line or tube 122. FIGS. 2 and 3 illustrate that disposable set 100 also includes a patient connector 134 connected to or in fluid communication with a distal end of patient line or tube 124. FIGS. 2 and 3 further illustrate that disposable set 100 includes a second dialysis fluid container or bag 136 connected to or in fluid communication with a distal end of second dialysis fluid container or bag line 126. FIGS. 2 and 3 illustrate that disposable set 100 still further includes a third dialysis fluid container or bag 138 connected to or in fluid communication with a distal end of third dialysis fluid container or bag line 128.

First fresh dialysis fluid/heating container or bag 132 as illustrated in FIGS. 2 and 3 is placed onto batch heater 34 for heating and onto temperature sensors 36a and 36b for temperature sensing. First fresh dialysis fluid/heating container or bag 132 may hold the same type and quantity of dialysis fluid as at least one of second and third containers or bags 136, 138. Alternatively, all three containers or bags may hold different types of dialysis fluids, e.g., different dextrose or glucose concentrations, and/or different quantities of same. Last container or bag 138 may for example hold a different formulation of dialysis fluid, e.g., icodextrin.

FIGS. 2 and 3 further illustrate drain line or tube 120 in operable communication with drain pinch valve 40, first fresh dialysis fluid/heating container or bag line or tube 122 in operable communication with fluid/heater pinch valve 42, patient line or tube 124 in operable communication with patient pinch valve 44, second dialysis fluid container or bag line 126 in operable communication with second fluid valve 46 and third dialysis fluid container or bag line 128 in operable communication with third fluid valve 48. Pinch valves 40, 42, 44, 46 and 48 are alternatively stopcock valves as described herein.

FIGS. 2 and 3 illustrate that cycler 20a of system 10 may provide additional sensors, such as air detection or prime sensors 32a and 32b located along first fresh dialysis fluid/ heating container or bag line or tube 122 and patient line or tube 124, respectively. Air detection or prime sensors 32a and 32b output to control unit 50 and may for example be light detection sensors, capacitance sensors, magnetic sensors or other types of sensors that can discern between air being present in the corresponding tube versus fresh or used dialysis fluid. Air detection sensor 32a operating with fresh dialysis fluid/heating container or bag line or tube 122 may be used for detecting air that comes out of solution during heating in first fresh dialysis fluid/heating container or bag 132 prior to delivery to patient P. Air detection or prime sensor 32b operating with patient line or tube 124 may be used for confirming that the patient line has been primed properly and for air alarms during fresh dialysis fluid delivery to patient P.

Table 1 below illustrates one example valve sequencing chart for the flow schematic of system 10 of FIG. 3, under control of control unit 50, in which valve 42 for first fresh dialysis fluid/heating container or bag line or tube 122 is located above valve 40 for drain line or tube 120. It should be appreciated that the valve sequencing for system 10 in FIG. 2, under control of control unit 50, is the same as the chart below, wherein the difference is that the valves would read instead left to right V40, V42, V44, V48, V46. The first three sequences are for priming and involve flowing fresh dialysis fluid through different combinations of lines and in different directions to remove air from disposable set 100. In priming sequence 1, control unit 50 causes drain valve 40 and dialysis fluid valves 46 and 48 to open and with the other valves closed actuates peristaltic pump actuator 30 in a clockwise direction (FIG. 3) for a defined number of strokes to pull fresh dialysis fluid from second and third dialysis fluid containers or bags 136, 138 to and to push same to drain 130, priming lines or tubes 126, 128, 108 and 120. In priming sequence 2, control unit 50 causes drain valve 40 and dialysis fluid valve 46 to open and with the other valves closed actuates peristaltic pump actuator 30 in a clockwise direction (FIG. 3) for another defined number of strokes to pull fresh dialysis fluid from second dialysis fluid container or bag 136 and to push same to drain 130, priming lines or tubes 126, 108 and 120.

psig (note that a higher psig limit, such as +9 psig may be restricted to certain points in the patient fill, e.g., during the middle portion). The flow profile may involve control unit 50 at the end of the patient fill lowering the positive pressure and flowrate, enabling a precise fill volume to be more easily achieved. It is believed that the patient is more sensitive to positive pumping pressure at the beginning and end of the patient fill, whereas the patient is less sensitive in the middle of the fill during which the patient's peritoneum is partially full and able to absorb higher pressures.

TABLE 1

| sequence | Lines | V42 | V40 | V44 | V46 | V48 | pump dir. |
|---|---|---|---|---|---|---|---|
| prime 1 | 138, 136 to drain 130 (defined strokes) | cl | op | cl | op | op | clock |
| prime 2 | 136 to drain 130 (defined strokes) | cl | op | cl | op | cl | clock |
| prime 3 | 132 to patient P (defined strokes with priming algorithm) | op | cl | op | cl | cl | counterclock |
| fill | 132 to patient P (flow profiling) | op | cl | op | cl | cl | counterclock |
| drain | Patient P to drain 130 (flow profiling) | cl | op | op | cl | cl | clock |
| heater | 136 to 132 or | op | cl | cl | op | cl | clock |
| replenish | 138 to 132 | op | cl | cl | cl | op | clock |

In priming sequence 3, control unit 50 causes dialysis fluid/heater valve 42 and patient line valve 44 to open and with the other valves closed actuates peristaltic pump actuator 30 in a counterclockwise direction (FIG. 3) for another defined number of strokes to pull fresh dialysis fluid from dialysis fluid/heater container or bag 132 and to push same to patient P, priming lines or tubes 122, 108 and 124. Along with the defined number of strokes (e.g., knowing patient line length and assumed volume pumped per stroke), or perhaps in place of the defined number of strokes, it is contemplated to position the end of patient line or tube 124 within a clip or other holder provided at housing 22 of cycler 20*a*, and which is adjacent to air detection or prime sensor 32*b*. When air detection or prime sensor 32*b* senses dialysis fluid instead of air, control unit 50 considers the priming of patient line or tube 124 to be complete or perhaps almost complete after which one or more additional pump stroke is made to ensure that the patient line is fully primed.

At the end of priming sequence 3, all lines of disposable set 100 have been primed. Priming sequences 1 to 3 also fully prime dialysis fluid chambers 114 of pressure sensing pods 112*a* and 112*b*. After priming, treatment may begin assuming that the fresh dialysis fluid within first fresh dialysis fluid/heating container 132 has been heated to body temperature. It is contemplated that the initial heating occur before and during priming sequences 1 to 3. Additionally, in many instances patient P is full of effluent at the start of treatment (from a prior treatment) so that after priming the first treatment step is a drain of patient P. The initial heating may accordingly also occur during an initial drain of patient P.

In the fill sequence of Table 1, control unit 50 causes dialysis fluid/heater valve 42 and patient line valve 44 to open (or remain open after priming sequence 3) and with the other valves closed actuates peristaltic pump actuator 30 in a counterclockwise direction (FIG. 3) according to a fill profile in one embodiment. One possible fill profile starts with control unit 50 causing peristaltic pump actuator 30 to operate at a low positive pressure and flowrate and to ramp up the fill flowrate after a certain initial fill percentage has been completed to a maximum fill flowrate, e.g., set by the maximum allowable patient fill pressure, e.g., +1 psig to +9

In the drain sequence of Table 1, control unit 50 causes drain valve 40 and patient line valve 44 to open and with the other valves closed actuates peristaltic pump actuator 30 in a clockwise direction (FIG. 3) according to a drain profile in one embodiment. One possible drain profile is similar to the example fill profile and starts with control unit 50 causing peristaltic pump actuator 30 to operate at a low negative pressure and flowrate and to ramp up the drain flowrate after a certain initial drain percentage has been completed to a maximum drain flowrate, e.g., set by the maximum allowable patient drain pressure, e.g., −1 psig to −3 psig. The drain profile may involve control unit 50 at the end of the patient drain lessening the negative pressure and flowrate, enabling a precise drain volume to be more easily achieved. Alternatively, the drain may end when a particular condition occurs, e.g., a negative pressure sensing of the patient being empty or effectively empty. As before with filling, it is believed that the patient is more sensitive to negative pumping pressure at the beginning and end of the patient drain, whereas patient P is less sensitive in the middle of the drain where the patient's peritoneum is partially full of effluent, which is able to absorb higher negative pressures.

In the heater replenish sequence of Table 1, control unit 50 causes a desired one of the second or third dialysis fluid container valves 46 or 48 and first dialysis fluid/heater container valve 42 to be open, and with the other valves closed actuates peristaltic pump actuator 30 in a clockwise direction (FIG. 3) for a defined number of strokes to pull fresh dialysis fluid from second or third dialysis fluid container or bag 136, 138 and push same to dialysis first fluid/heater container or bag 132. The defined number of strokes here may correspond to a subsequent patient fill volume, perhaps with some additional amount of fluid as an engineering factor and for tubing volume. It is contemplated that the heater replenish sequence occur directly after the completion of a patient fill and/or during a patient dwell to provide enough time for the fresh dialysis fluid replenish volume to be heated to body temperature, e.g., e.g., 37° C.

In addition to the valve sequencing discussed above in connection with Table 1, control unit 50 may further additionally be programmed to vary the speed of peristaltic pump actuator 30 to perform a patient fill according to a fill profile in which the speed of the peristaltic pump actuator operating in the filling direction is increased during a middle portion of the patient fill. Control unit 50 may still further additionally be programmed to perform a patient drain according to a drain profile in which the speed of peristaltic pump actuator 30 operating in the draining direction is increased during a middle portion of the patient drain. In any case, the peristaltic pumping system of the present disclosure provides a wide range of flowrates, e.g. from less than 10 mL/min to greater than 350 mL/min, while ensuring that positive and negative patient pressures are within limits. The peristaltic pumping is also relatively smooth due to pressure sensing pods 112a and 112b as discussed herein, allowing for minimal flow pulsation across treatment.

The priming sequence discussed in connection with Table 1 is for a valve arrangement in which there is independent control of each valve 42 to 48. FIGS. 2 and 3 illustrate dashed boxes around valves 40 and 42 and valves 44 and 46 to show an alternative embodiment mentioned above in which the pinch valves are "3 by 2" pinch valves, which use a single motor and have two tubes running through the valve such that one tube is open while the other is closed, and wherein the states can be reversed. "3 by 2" pinch valves are incapable of opening or closing both tubes at the same time. The priming sequence using "3 by 2" pinch valves, e.g., in combination with a single pinch valve to provide five different line closures for the five lines 120 to 128, may require a slightly different priming flowpath over the six sequences illustrated in Table 1. The overall result however is the same, which is a fully primed disposable set at the beginning of treatment.

Figure 4A:
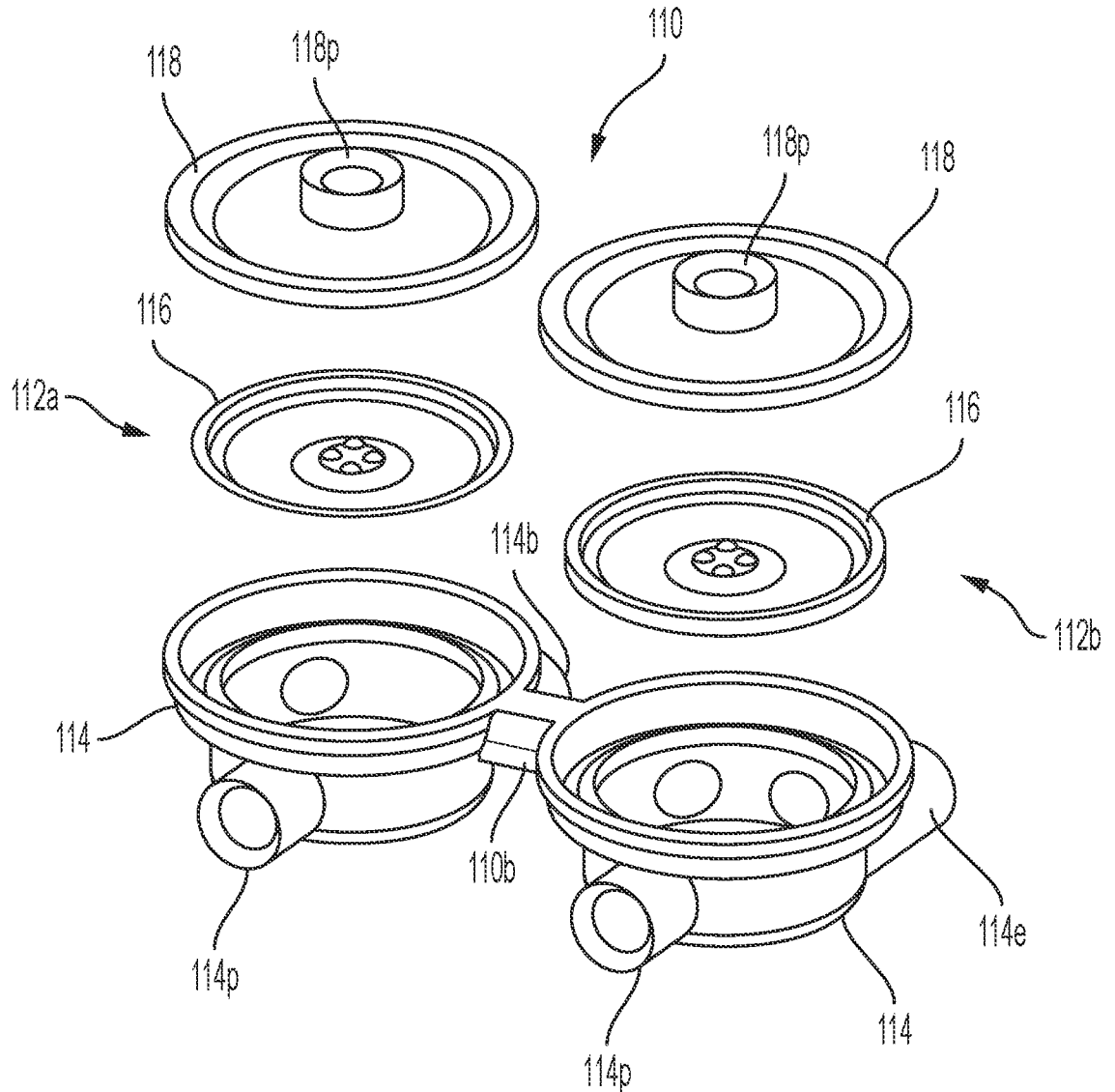
FIGS. 4A and 4B are perspective views of one embodiment of a disposable set for use with the peristaltic pump-based system of the present disclosure.
Figure 4B:
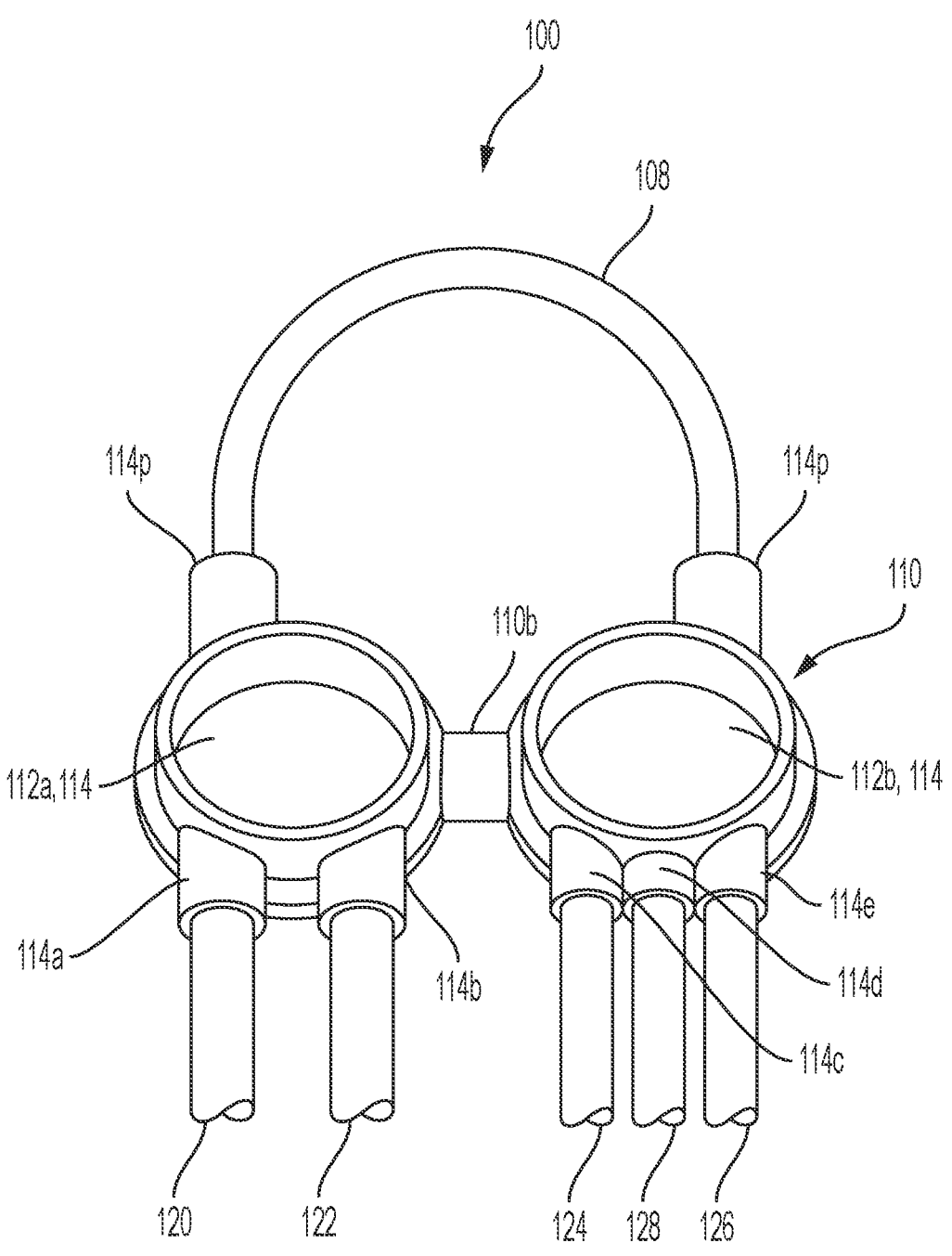

Referring now to FIGS. 4A and 4B, rigid manifold 110 and pressure sensing pods 112a and 112b are illustrated in more detail. FIG. 4A is an exploded view showing the different components of pressure sensing pods 112a and 112b, wherein each component may be made of any of the materials discussed herein. FIG. 4A also illustrates that pressure sensing pods 112a and 112b may form a single rigid manifold 110 via bridging member 110b. Pressure sensing pods 112a and 112b in the illustrated embodiment are made of three primary pieces, namely, a dialysis fluid chamber 114 that carries fresh or used dialysis fluid, a diaphragm 116 that flexes based on fluid pressure, and a transmission fluid chamber 118 that holds a pressure transmission fluid, such as air that is compressed corresponding to the positive or negative pumping pressure applied to the fresh or used dialysis fluid. The pressure transmission fluid contacts pressure transducers 26 and 28 that output corresponding pressure signals to control unit 50. In one embodiment, dialysis fluid chambers 114 are sealingly fixed to transmission fluid chambers 118, e.g., via ultrasonic sealing, heat sealing or adhesive sealing, in such a way that diaphragms 116 are sealed in place so that dialysis fluid is prevented from entering transmission fluid chambers 118 and transmission fluid is prevented from entering dialysis fluid chambers 114.

In the illustrated embodiment, bridging member 110b extends between dialysis fluid chambers 114 such that dialysis fluid chambers 114 of both pressure sensing pods 112a and 112b may be made, e.g., molded, as a single unitary piece. Bridging member 110b may alternatively extend between transmission fluid chambers 118 such that the transmission fluid chambers may be made as a single unitary piece. Transmission fluid chambers 118 are each provided with a transmission fluid port 118p that may be configured to connect directly with one of pressure transducers 26 and 28 or to connect to the transducers via intermediary tubes (not illustrated).

FIGS. 4A and 4B illustrate that dialysis fluid chambers 114 of disposable set 100 are each provided with, e.g., formed with a peristaltic pumping port 114p, which sealingly attaches to an end of peristaltic pumping tube 108. Dialysis fluid chamber 114 of pressure sensing pod 112a includes tubing ports 114a and 114b, which sealingly attach to an end of drain line or tube 120 and first fresh dialysis fluid/heating container or bag line or tube 122, respectively. Dialysis fluid chamber 114 of pressure sensing pod 112b includes tubing ports 114c, 114d and 114e that sealingly attach to an end of patient line or tube 124, third dialysis fluid container or bag line 128, and second dialysis fluid container or bag line 126, respectively, in the illustrated embodiment, which corresponds to the tubing orientation of FIG. 2 (versus FIG. 3).

Figure 4C:
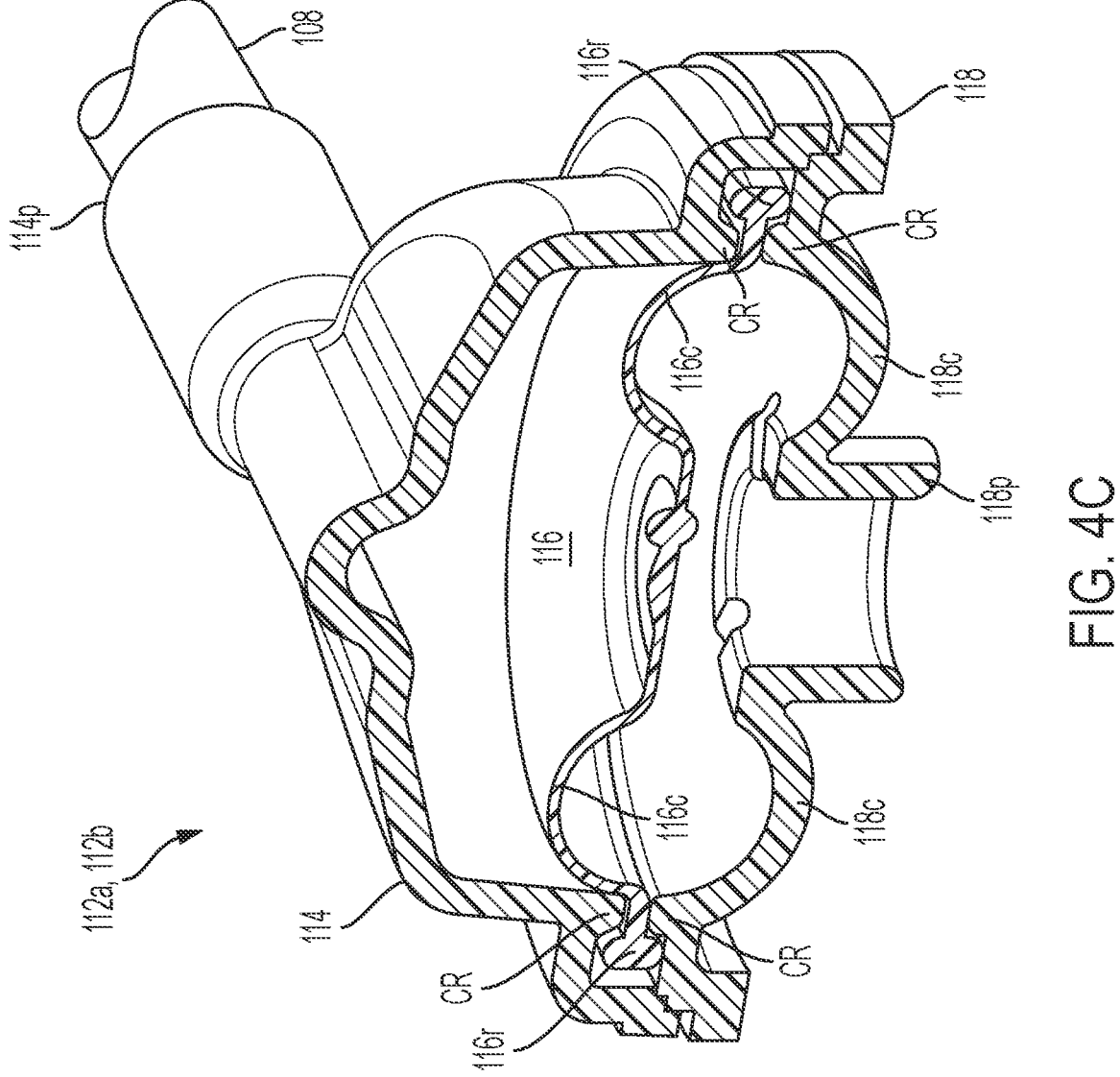
FIG. 4C is a sectioned perspective view of one embodiment of an assembled pressure sensing pod of FIGS. 4A and 4B.

FIG. 4C illustrates one embodiment of an assembled pressure sensing pod 112a or 112b. Dialysis fluid chamber 114 of pressure sensing pod 112a or 112b includes peristaltic tubing port 114p, which sealingly attaches to an end of peristaltic pumping tube 108. Dialysis fluid chamber 114 in the illustrated embodiment is ultrasonically, heat or adhesively sealed to transmission fluid chamber 118 in a manner so as to hold flexible diaphragm 116 sealingly in place. In the illustrated embodiment, dialysis fluid chamber 114 and transmission fluid chamber 118 include or define mating crimping rings CR that pinch flexible diaphragm 116 in a circular manner just inside of a thickened outer ring 116r of flexible diaphragm 116. Flexible diaphragm 116 as illustrated may be formed with one or more prestressed or preformed shapes, such as a preformed circular channel 116c. Transmission fluid chamber 118 may likewise include or be formed with circular channel 118c encircling transmission fluid port 118p, wherein circular channel 118c is aligned with circular channel 116c

Figure 5A:
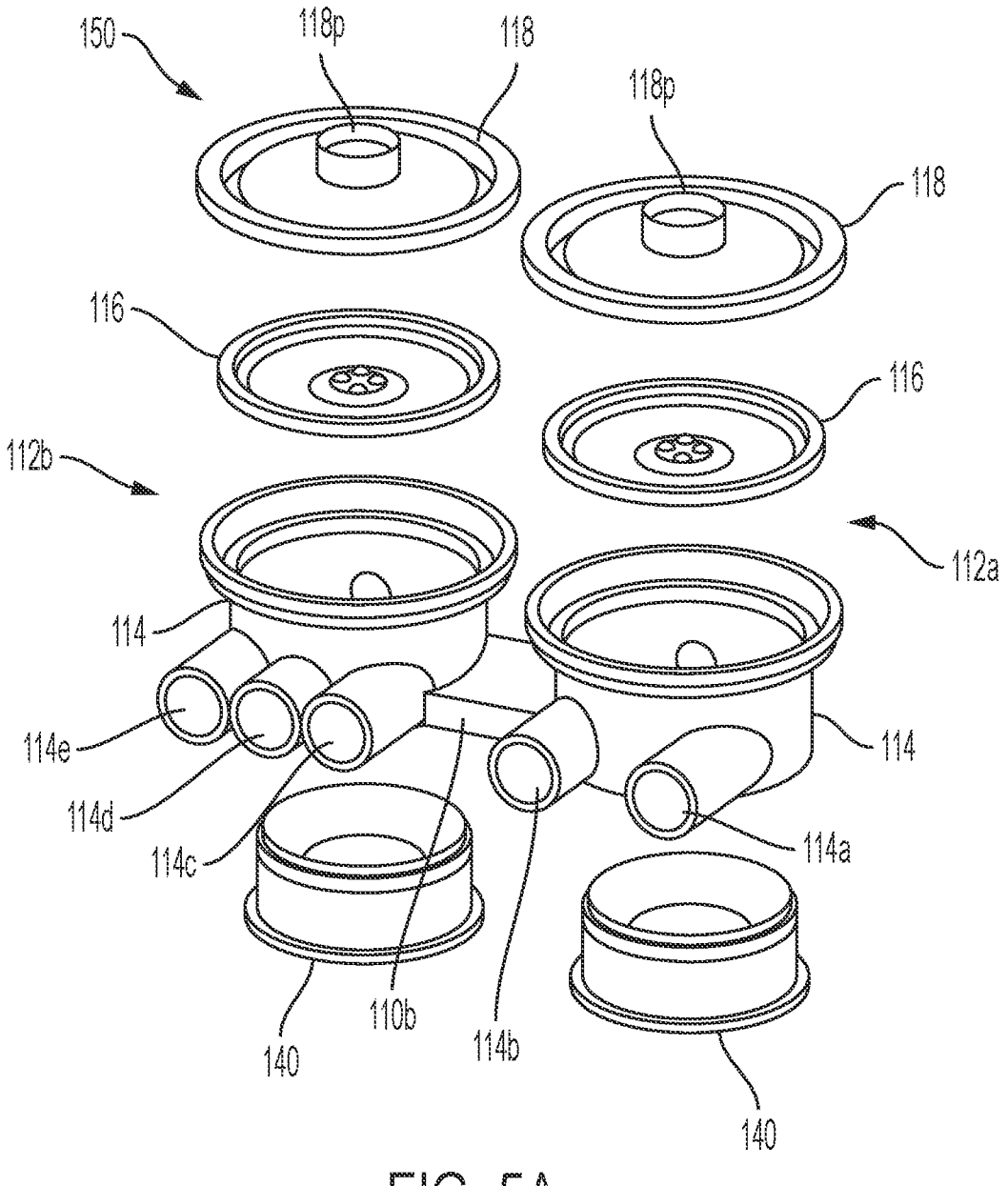
FIGS. 5A and 5B are perspective views of another embodiment of a disposable set for use with the peristaltic pump-based system of the present disclosure.
Figure 5B:
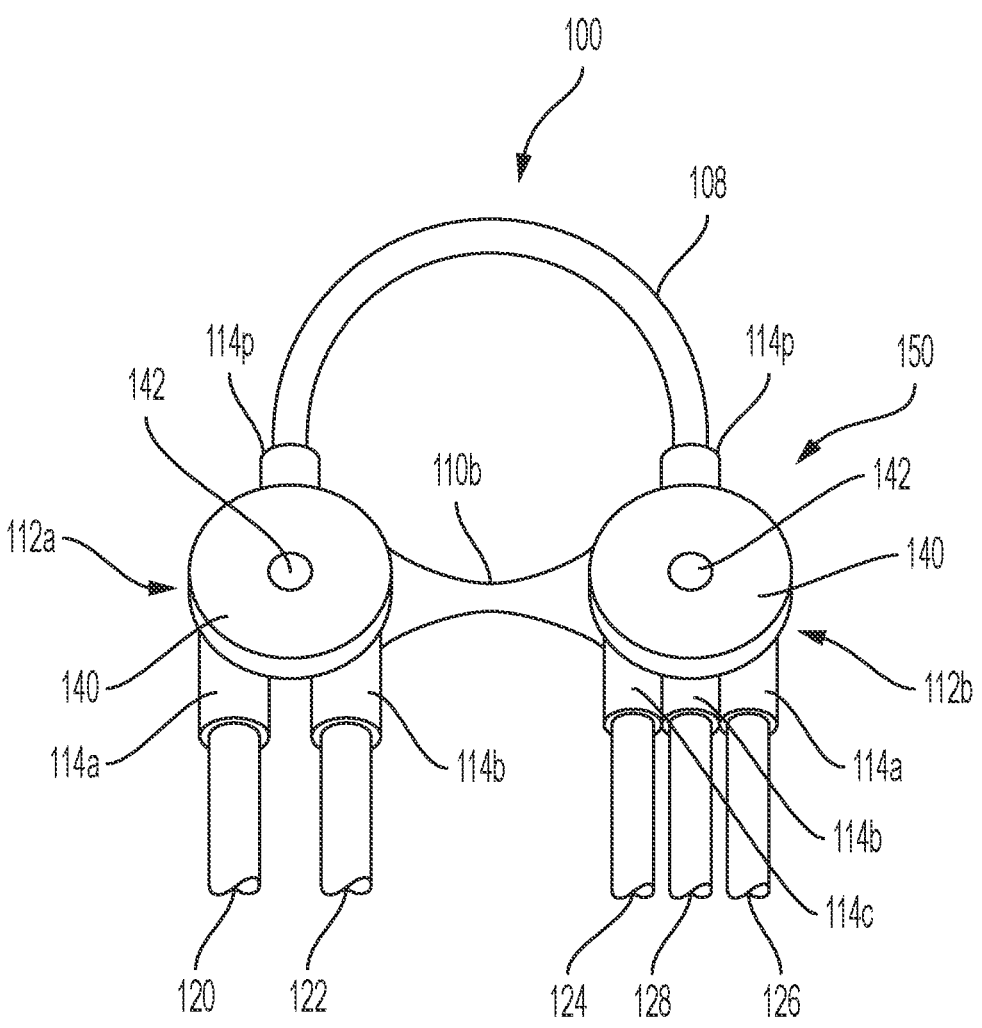

FIGS. 5A and 5B illustrate an alternative embodiment for disposable set 100, which uses an alternative rigid manifold 150, wherein dialysis fluid chambers 114 are modified to operate with stopcock handles 140. Otherwise, diaphragms 116, transmission fluid chambers 118, the fixing of dialysis fluid chambers 114 to transmission fluid chambers 118, and the arrangement of ports 114a to 114e and 114p and their connection to tubes 120, 122, 124, 128, 126 and 108 are the same as described above for FIGS. 4A and 4B in one embodiment. Stopcock handles 140 are driven by multiway or stopcock valve actuators, which are located within cycler 20a in a manner similar to that illustrated for valves 40, 42, 44, 46 and 48, except that rigid manifold 110 is placed directly onto the multiway or stopcock valve actuators when loading disposable set 100 for treatment. Stopcock handles 140 include a driving aperture 142 that accepts a driving rod 144 (see FIG. 11A) of the stopcock valve actuators 146 and 148 (see FIG. 11A), e.g., via a keyed relationship. Control unit 50 causes the driving rods of the stopcock valve actuators to rotate to a desired angular position to allow fluid flow to or from a desired line or tube 120, 122, 124, 126 or 128.

For pressure sensing pod 112a, control unit 50 causes the multiway or stopcock valve actuator to rotate stopcock handle 140 between three positions, one in which peristaltic pumping tube 108 communicates fluidly with drain line or tube 120, another in which peristaltic pumping tube 108 communicates fluidly with first fresh dialysis fluid/heating container or bag line or tube 122, and a third in which all lines are occluded. For pressure sensing pod 112b, control unit 50 causes the multiway or stopcock valve actuator to rotate stopcock handle 140 between four positions, one in which peristaltic pumping tube 108 communicates fluidly with patient line or tube 124, a second in which peristaltic pumping tube 108 communicates fluidly with second dialysis fluid container or bag line 126, a third in which peristaltic pumping tube 108 communicates fluidly with third dialysis fluid container or bag line 128, and a fourth in which all lines are occluded. The all lines occluded positions of the two stopcock valves enable flexible membranes 116 to be desirably positioned within chambers 114 and 118 so as to provide an accurate pressure signal over a desired range of positive and negative pressures to be measured.

It should be appreciated that there are other ways to actuate stopcock handles 140 besides the use of driving apertures 142 and mating driving rods. For example, the outer diameter of stopcock handle 140 may include gear teeth or ratchets that mate with gear teeth or ratchets of a driver that drives stopcock handle 140 from the outside.

Figures 6, 7:
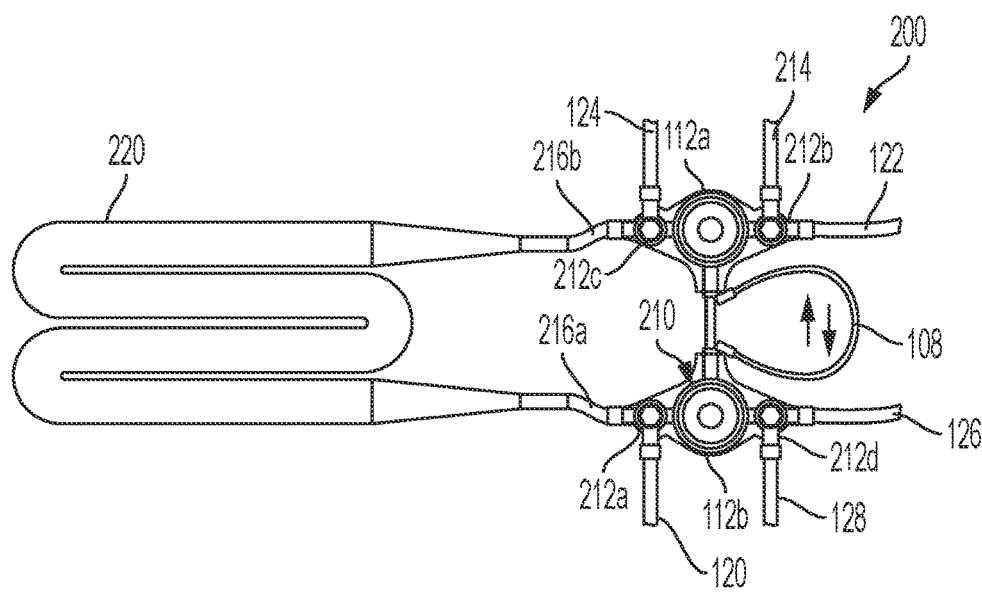
FIG. 6 is a top plan view of an alternative disposable set of the present disclosure using inline heating and stopcock valves.
FIG. 7 is a perspective view of one alternative APD cycler configuration for the peristaltic pump-based system of the present disclosure.

Referring now to FIG. 6, an alternative rigid manifold 210 of an alternative disposable set 200 for use with system 10 is illustrated. Alternative rigid manifold 210 includes four multiway or stopcock valves 212a to 212d (each having an all lines occluded position in one embodiment), which here are not integrated with pressure sensing pods 112a and 112b. It is accordingly contemplated for any version of system 10 to provided stopcock valves separately or in combination with pressure sensing pods 112a and 112b. Multiway or stopcock valves 212a to 212d operate with four respective multiway or stopcock valve actuators (not illustrated but part of the cycler) under control of control unit 50. Stopcock valve 212a is rotatable to allow fresh dialysis fluid to flow from manifold 210 into a heater inlet tube 216a or from manifold 210 to drain tube 120 (to either a drain container or house drain). Stopcock valve 212d is rotatable to allow fresh dialysis fluid to flow from either a second dialysis fluid dialysis fluid container line or tube 126 into manifold 210 or from a third dialysis fluid dialysis fluid container line or tube 128 into manifold 210. Stopcock valve 212b is rotatable to allow fresh dialysis fluid to flow from either a first dialysis fluid dialysis fluid container line or tube 122 into manifold 210 or from a fourth or last fill container line 214 into manifold 210 (disposable set 200 accordingly allows for an extra container of fresh dialysis fluid). Stopcock valve 212c is rotatable to allow heated dialysis fluid to flow from a heater outlet tube 216b into patient line 124 or used dialysis fluid to flow from patient line 124 into manifold 210.

Alternative rigid manifold 210 also includes an inline fluid heating pathway 220, e.g., serpentine, which is placed in operable communication with an inline heater (not illustrated) under control of control unit 50, wherein the inline heater may be integrated with the cycler of system 10 or may be provided as a standalone unit as part of system 10. In a standalone implementation, the standalone inline heater may include its own control unit, which may operate as a delegate control unit to cycler control unit 50, wherein the two control units may communicate in a single direction or bidirectionally in a wired or wireless manner. One or more temperature sensor 36a and 36b outputting to control unit 50 may be provided for use as feedback to control the inline heater to output heated, fresh dialysis fluid into heater outlet tube 216b and patient line 124 at body temperature or 37° C. Control unit 50 may employ a proportional, integral, derivative ("PID") control algorithm using feedback from one or more temperature sensor 36a and 36b to determine how much current or power to deliver to the inline heater.

Peristaltic pumping tube 108 is actuated via peristaltic pump actuator 30 under control of control unit 50 in a clockwise manner to pull used dialysis fluid from patient line 124 past pressure sensing pod 112a and to push same past pressure sensing pod 112b, and into drain line 120 to a drain container or house drain. Pressure sensing pods 112a and 112b dampen pulsatility and increase the accuracy of effluent or used dialysis fluid flow as discussed herein. Peristaltic pumping tube 108 is actuated via peristaltic pump actuator 30 under control of control unit 50 in a clockwise manner to pull fresh dialysis fluid from dialysis fluid container line 122 or fourth or last fill container line 214 past pressure sensing pod 112a and to push same past pressure sensing pod 112b, through inline heating pathway 220 where the fresh fluid is heated, and into patient line 124 to the patient. Pressure sensing pods 112a and 112b again dampen pulsatility and increase the accuracy of fresh, heated dialysis fluid flow as discussed herein.

Peristaltic pumping tube 108 is actuated via peristaltic pump actuator 30 under control of control unit 50 in a counterclockwise manner to pull fresh dialysis fluid from second and third dialysis fluid container tubes or lines 126 and 128 past pressure sensing pod 112b and to push same past pressure sensing pod 112a and into the first dialysis fluid container line or tube 124 in preparation for a next patient fill. The fill preparation movement of fresh dialysis fluid may be performed during a patient dwell. Pressure sensing pods 112a and 112b again dampen pulsatility, however, because the patient is not involved in the fill preparation pumping procedure, the operating pressures and corresponding flowrates may be higher. System 10 of FIG. 6 is further advantageous because, as discussed above, it allows for a fourth container of fresh dialysis fluid, which in addition to the last fill solution (e.g., icodextrin), may be the same or different type of fresh dialysis fluid as the first and second containers of dialysis fluid.

Referring now to FIG. 7 an alternative configuration for the cycler of system 10 is illustrated via cycler 20b. Cycler 20b is similar to cycler 20a of FIG. 1 in that peristaltic pump actuator 30, pressure transducers 26 and 28 and pinch valves 40 to 48 are oriented such that pressure sensing pods 112a and 112b and tubes or lines 120 to 128 of rigid manifold 110 are oriented horizontally. The primary difference is that peristaltic pump actuator 30, pressure transducers 26 and 28 and pinch valves 40 to 48 instead of being located within cycler 20a as in FIG. 1, are located instead on top of cycler 20b in FIG. 7. A lightweight metal or plastic (e.g., clear acrylic) lid 38 may be provided, e.g., hinged to the housing of cycler 20b, for easy access to peristaltic pump actuator 30, pressure transducers 26 and 28 and pinch valves 40 to 48 for the ready loading of disposable set 100. While door or lid 38 does not have to be structurally capable of handling pinch valve forces, which is an advantage of cycler 20b, door or lid 38 is however structurally sound enough to enable positioners provided by the lid to push disposable tubes or lines into respective pinch slots.

User interface 58 may be located along any desired surface of the housing of cycler 20b or rotate up into position via a mounting arm hinged to cycler 20b. Once disposable set 100 is loaded, lid 38 may be closed so that treatment may begin.

Another difference between cyclers 20a and 20b is that cycler 20a includes an integrated heater 34. Cycler 20b instead includes a standalone or modular heater (not illustrated), which may be a batch or inline heater. If a batch heater, initial dialysis fluid container or bag 132 disposable set 100 is loaded onto the batch heater for treatment. If an inline heater, inline fluid heating pathway 220, e.g., serpentine, is loaded instead onto the inline heater for treatment. In either case, the standalone or modular heater enables cycler 20b to be very compact, e.g., on the order of 214 mm (8.4 inches) and 175 mm (6.9 inches) in footprint by 110 mm (4.3 inches) in height, including lid 38.

Figures 8A, 8B, 9:
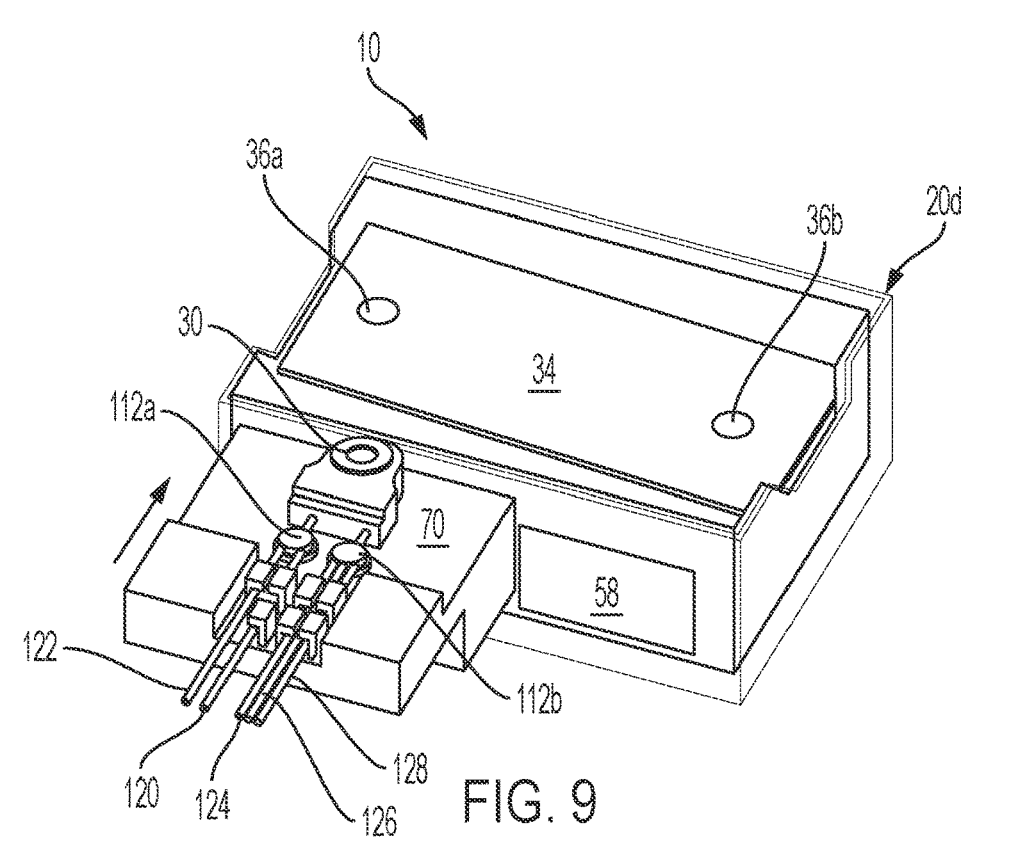
FIGS. 8A and 8B are perspective views of another alternative APD cycler configuration for the peristaltic pump-based system of the present disclosure.
FIG. 9 is a perspective view of a further alternative APD cycler configuration for the peristaltic pump-based system of the present disclosure.

Referring now to FIGS. 8A and 8B another alternative configuration for the cycler of system 10 is illustrated via cycler 20c. Cycler 20c is very similar to that of cycler 20b of FIG. 7 in that peristaltic pump actuator 30, pressure transducers 26 and 28 and the valve actuators are oriented such that pressure sensing pods 112a and 112b and tubes or lines 120 to 128 of rigid manifold 150 are oriented horizontally. Another similarity is that peristaltic pump actuator 30, pressure transducers 26 and 28 and the valve actuators are again located on top of cycler 20c in FIG. 7. A small, lightweight metal or plastic cover 66 may be provided, e.g., hinged, to the housing of cycler 20c, for easy access to peristaltic pump actuator 30, pressure transducers 26 and 28 and pressure sensing pods 112a and 112b for the ready loading of rigid manifold 150. User interface 58 in the illustrated embodiment rotates up into position via a mounting arm 68 hinged to cycler 20b. Once disposable set 100 is loaded, cover 66 may be closed so that treatment may begin. For improved usability, it is contemplated for cover 66 to include or provide a moveable, e.g., slideable, peristaltic pump race to make the loading of pump tubing segment 108 easier. Cyclers 20b and 20c also include a standalone or modular heater (not illustrated), which may be a batch or inline heater. If a batch heater, initial dialysis fluid container or bag 132 disposable set 100 is loaded onto the batch heater for treatment. If an inline heater, inline fluid heating pathway 220, e.g., serpentine, is loaded instead onto the inline heater for treatment.

The primary difference between cycler 20c and cycler 20b is that instead of pinch valves, cycler 20c uses the multiway or stopcock valve version of alternative rigid manifold 150 illustrated in connection with FIGS. 5A and 5B. To load alternative rigid manifold 150, the user sets stopcock handles 140 (see FIGS. 5A and 5B) onto multiway or stopcock valve actuators (see FIG. 11A), which are located at the top of cycler 20c. The user then stretches peristaltic pumping tube 108 over peristaltic pump actuator 30. Alternatively, control unit 50 may cause peristaltic pump actuator 30 to translate into operable position against peristaltic pumping tube 108. In either case, the user then closes cover 66 over alternative rigid manifold 150. Pressure sensing pods 112a and 112b associated with stopcock handles 140 operate respectively with lines or tubes 120 and 122 and 124, 126 and 128 as illustrated in FIGS. 5B, 8A and 8B.

Referring now to FIG. 9, a further alternative configuration for the cycler of system 10 is illustrated via cycler 20d. Cycler 20d is very similar to that of cycler 20a in that peristaltic pump actuator 30, pressure transducers 26 and 28 and pinch valves 40 to 48 are oriented such that pressure sensing pods 112a and 112b and tubes or lines 120 to 128 of rigid manifold 110 are oriented horizontally. Cyclers 20d and 20a also each include an integrated batch heater 34 and associated temperature sensors 36a and 36b under control of and outputting to control unit 50. Batch heater 34 is oriented differently with cycler 20d, which may help reduce the footprint of cycler 20d. Batch, e.g., resistive, heater in any embodiment may be angled so that dialysis fluid container 132 is tilted to allow air to migrate up into the back of the container.

Cycler 20d includes a tray 70 onto which peristaltic pump actuator 30, pressure transducers 26 and 28 and pinch valves 40 to 48 are placed so such that disposable set 100 including pressure sensing pods 112a and 112b and tubes or lines 120 to 128 of rigid manifold 110 may be loaded for treatment, after which tray 70 is translated into the housing of cycler

20d. At the end of treatment, tray 70 is slideably opened to remove the used disposable set. While cycler 20d is illustrated using pinch valves 40 to 48, cycler 20d may alternatively use multiway or stopcock valves described herein.

Figure 10:
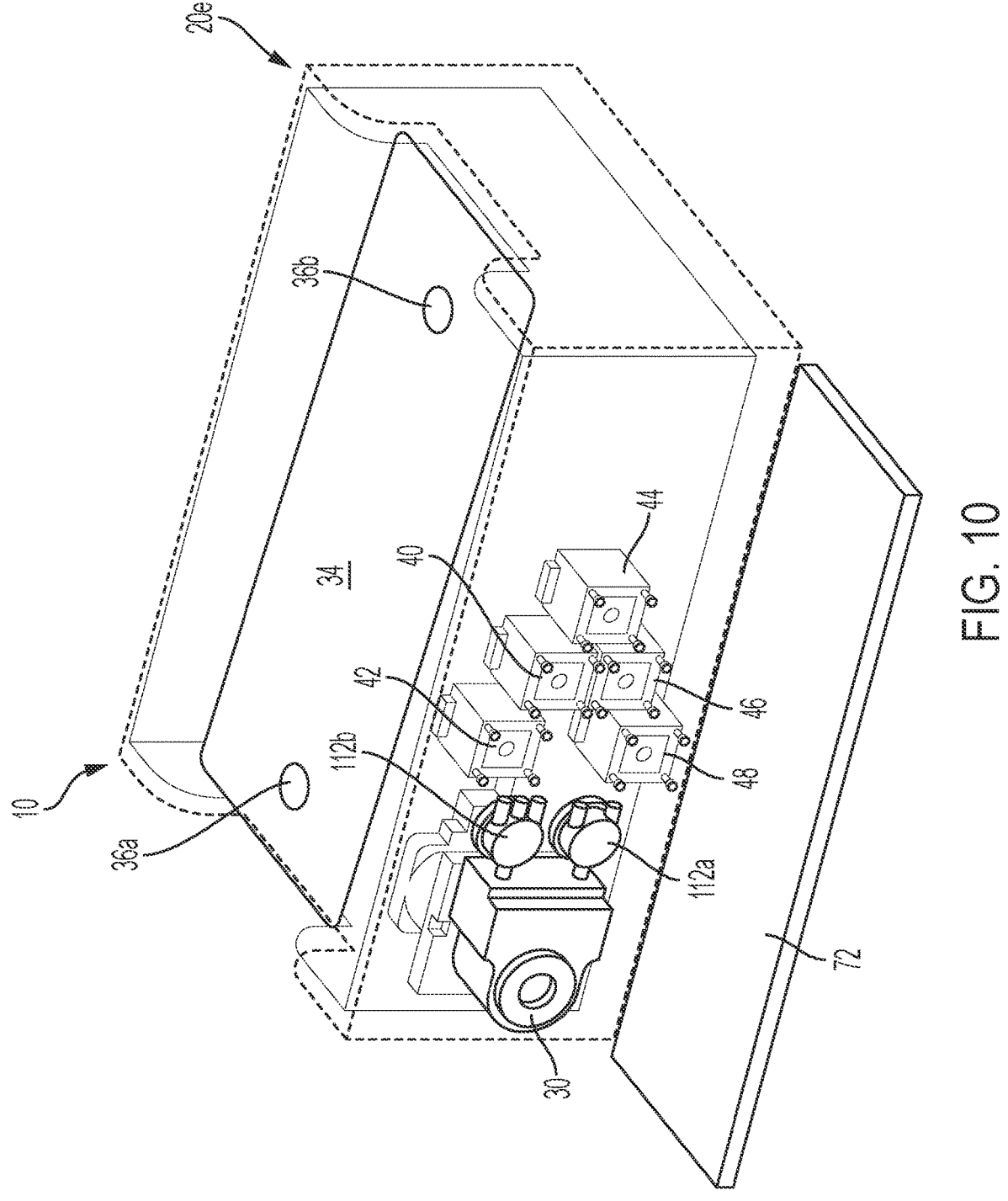
FIG. 10 is a perspective view of yet another alternative APD cycler configuration for the peristaltic pump-based system of the present disclosure.

Referring now to FIG. 10, yet another alternative configuration for the cycler of system 10 is illustrated via cycler 20e. Cycler 20e is similar to that of cycler 20d in that cyclers 20e and 20d also each include an integrated batch heater 34 and associated temperature sensors 36a and 36b under control of and outputting to control unit 50. Batch heater 34 is oriented the same as with cycler 20d, which may help reduce the footprint of the cycler.

With cycler 20e, peristaltic pump actuator 30, pressure transducers 26 and 28 and pinch valves 40 to 48 are oriented such that pressure sensing pods 112a and 112b and associated tubes or lines 120 to 128 of rigid manifold 110 are oriented instead vertically. The vertical orientation may help with air mitigation. A vertically opened and closed door 72, e.g., hinged to cycler 20e, may be closed once disposable set 100 (not illustrated) is loaded vertically into operation with peristaltic pump actuator 30, pressure transducers 26 and 28 and pinch valves 40 to 48 for treatment. Door 72 is opened when treatment is completed so that the used disposable set may be removed. While cycler 20e is illustrated using pinch valves 40 to 48, cycler 20e may alternatively use multiway or stopcock valves described herein.

Figure 11A:
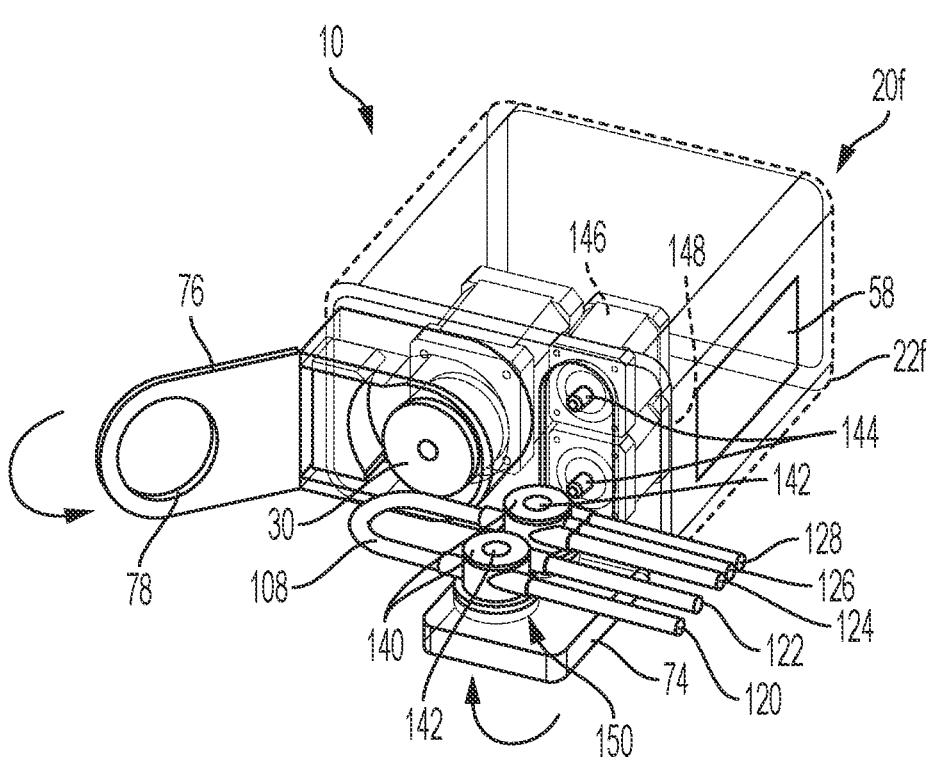
FIGS. 11A and 11B are perspective and front elevation views of yet a further alternative APD cycler configuration for the peristaltic pump-based system of the present disclosure.
Figure 11B:
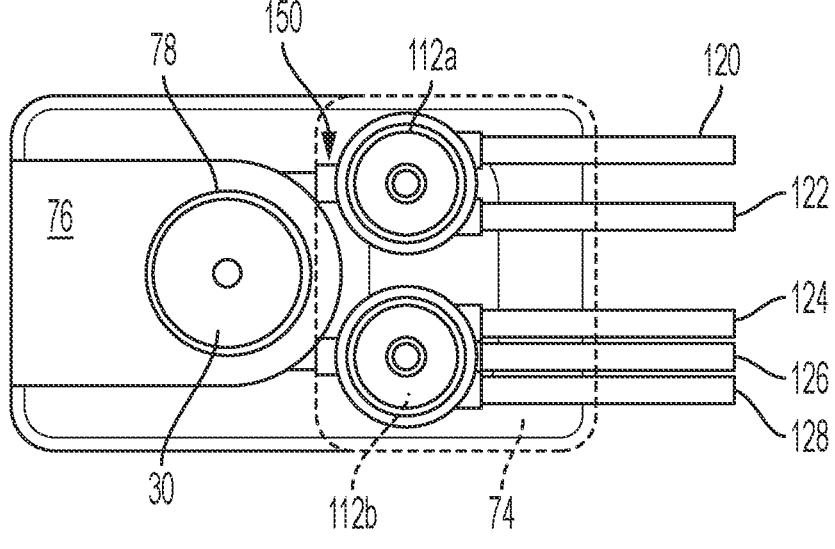

Referring now to FIGS. 11A and 11B, cycler 20f illustrates an alternative vertically oriented disposable set embodiment using alternative stopcock rigid manifold 150 illustrated in connection with FIGS. 5A and 5B. Alternative stopcock rigid manifold 150 includes disposable stopcock handles 140 having driving apertures 142 that accept cycler driving rods 144 of stopcock valve actuators 146 and 148 under control of control unit 50, e.g., via a keyed relationship. Control unit 50 causes driving rods 144 of the stopcock valve actuators 146 and 148 to rotate to a desired angular position to allow fluid flow to or from a desired line or tube 120, 122, 124, 126 or 128.

Cycler 20f in the illustrated embodiment includes two doors, a horizontally hinged valve door 74 and a vertically hinged pump door 76, which may be provided with a cutout 78, e.g., circular cutout, which extends over pump peristaltic actuator 30. To load stopcock rigid manifold 150, the user opens doors 74 and 76 and places rigid stopcock manifold 150 onto valve door 74 so that pressure sensing pods 112a and 112b are seated in fitted pod seats (not illustrated) located on the inside of valve door 74. The user then rotates door 74 up so that driving apertures 142 of stopcock handles 140 come into registry with driving rods 144 of stopcock valve actuators 146 and 148. The valves of cycler 20f are thereafter operational.

Rotating door 74 up (door 74 shown in phantom line in FIG. 11B to see pressure sensing pods 112a and 112b in solid line) also rotates peristaltic pumping tube 108 into close proximity to peristaltic pump actuator 30. In one embodiment, the user then stretches peristaltic pumping tube 108 over peristaltic pump actuator 30. Alternatively, control unit 50 may cause peristaltic pump actuator 30 to translate into operable position against peristaltic pumping tube 108. In either case, once peristaltic pumping tube 108 is loaded for operation against peristaltic pump actuator 30, the user closes pump door 76, so that cutout 78 moves into registry with peristaltic pump actuator 30. A further option is to provide a moveable raceway, e.g., as pump door 76 swings out or open, the raceway of the pump head moves accordingly to increase the clearance between the rollers of peristaltic pump actuator 30 and the raceway. As pump door 76 swings in or closes, the raceway closes onto the loaded peristaltic pumping tube 108.

In an embodiment, cutout 78 is covered with glass or clear acrylic so that the rotation of peristaltic pump actuator 30 may be viewed but cannot be touched. Doors 74 and 76 as illustrated may overlap each other.

Figure 12:
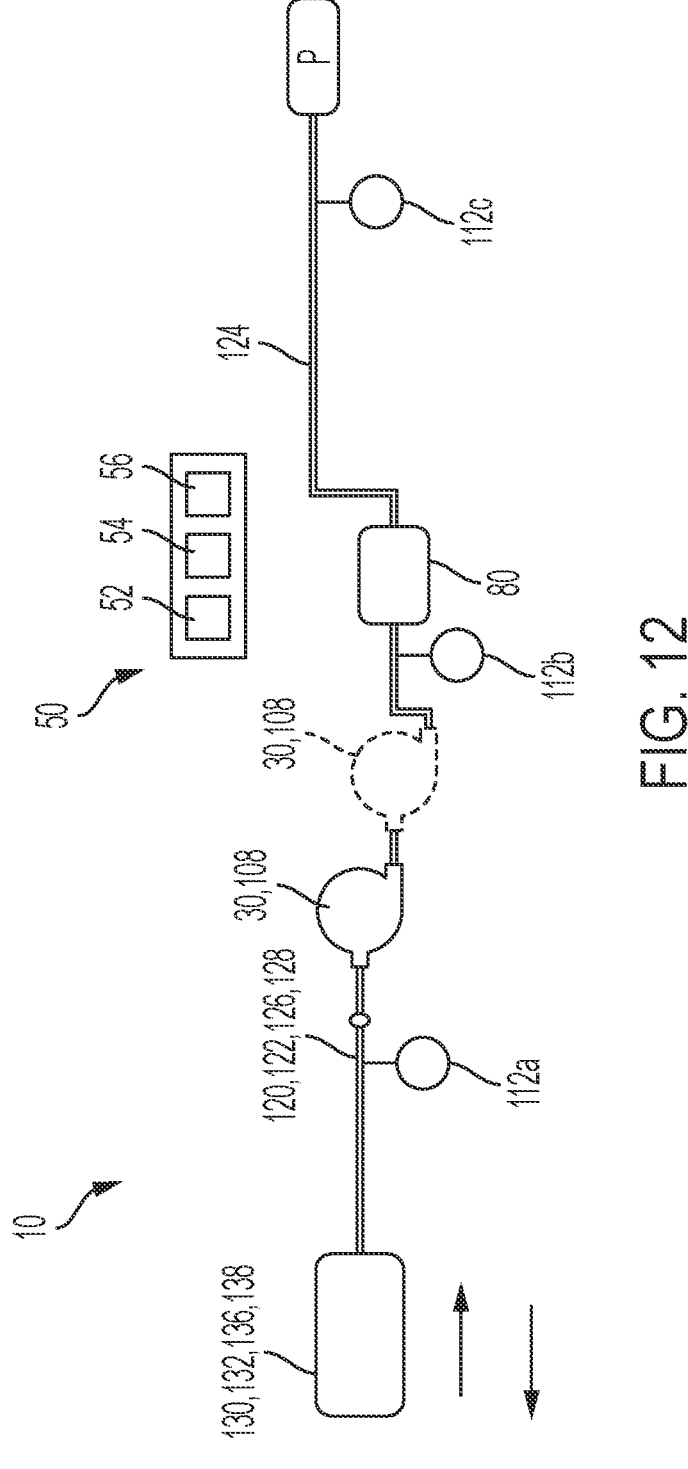
FIG. 12 is a front elevation view of a simplified flow schematic for use with any of the cycler configurations of the present disclosure, which includes the addition of a flow sensor for monitoring and/or controlling flowrate and volume of dialysis fluid delivered, and the optional addition of a second peristaltic pump.

FIG. 12 illustrates a simplified version of system 10, which includes drain container 130 and dialysis fluid containers or bags 132, 136 and 138 and associated tubes or lines 120, 122, 126 and 128 leading respectively from or to peristaltic pumping tube 108 operating with peristaltic pump actuator 30. Pressure sensing pods 112a and 112b are also illustrated. Patient line 124 leads from peristaltic pumping tube 108 to patient P. A flow sensor 80 is located along patient line 124 and outputs to control unit 50. System 10 may also include a downstream patient pressure sensor 112c that outputs to control unit 50.

Flow sensor 80 in an embodiment is an inline flow sensor, which may be an invasive disposable flow sensor or a reusable or durable flow sensor that is non-invasive. In either case, the output of flow sensor to control unit 50 may be integrated over time to monitor and determine accurately how much fresh dialysis fluid has been delivered to the patient and how much used dialysis fluid has been removed from the patient. Control unit 50 may also calculate a difference between the two, which is the patient's removed ultrafiltration ("UF") volume. Flow sensor 80 is also used in connection with the charts below to output dialysis fluid flowrate. Thus while a goal of system 10 is to make peristaltic pumping inherently accurate, it is also contemplated to add a volume and flowrate monitoring and control device, such as a flow sensor 80 operating with control unit 50.

FIG. 12 also illustrates that any of cyclers 20a to 20f of system 10 may optionally include a second peristaltic pump actuator 30 and associated peristaltic pumping tube 108. The outlet pressure of the upstream peristaltic pump actuator 30 and associated peristaltic pumping tube 108 (depending on if flow is fresh dialysis fluid from left to right or used dialysis fluid from right to left) is used to set a desired positive pressure on the inlet side of the downstream peristaltic pump 30/108. Doing so removes variability at the inlet side of the downstream peristaltic pump 30/108 and thus improves peristaltic pumping accuracy. That is, the serial placement of peristaltic pumps 30/108 ensures that the pressure boundary conditions of the downstream peristaltic pump 30/108 are consistent, which increases accuracy. Control unit 50 selects the revolutions per minute ("RPM") of the upstream peristaltic pump 30/108 as a function of the RPM of the downstream peristaltic pump 30/108 in one embodiment. RPM's of the upstream peristaltic pump may be a (i) constant function, e.g., $RPM_{upstream}$=f ($RPM_{downstream}$), where $RPM_{downstream}$ is determined by a set flowrate or a (ii) periodic function, e.g., $RPM_{upstream}$=a sin($2\pi f^*t$)+b+$RPM_{downstream}$, where a is periodic function amplitude, f is frequency, and b is a constant offset.

Figure 13:
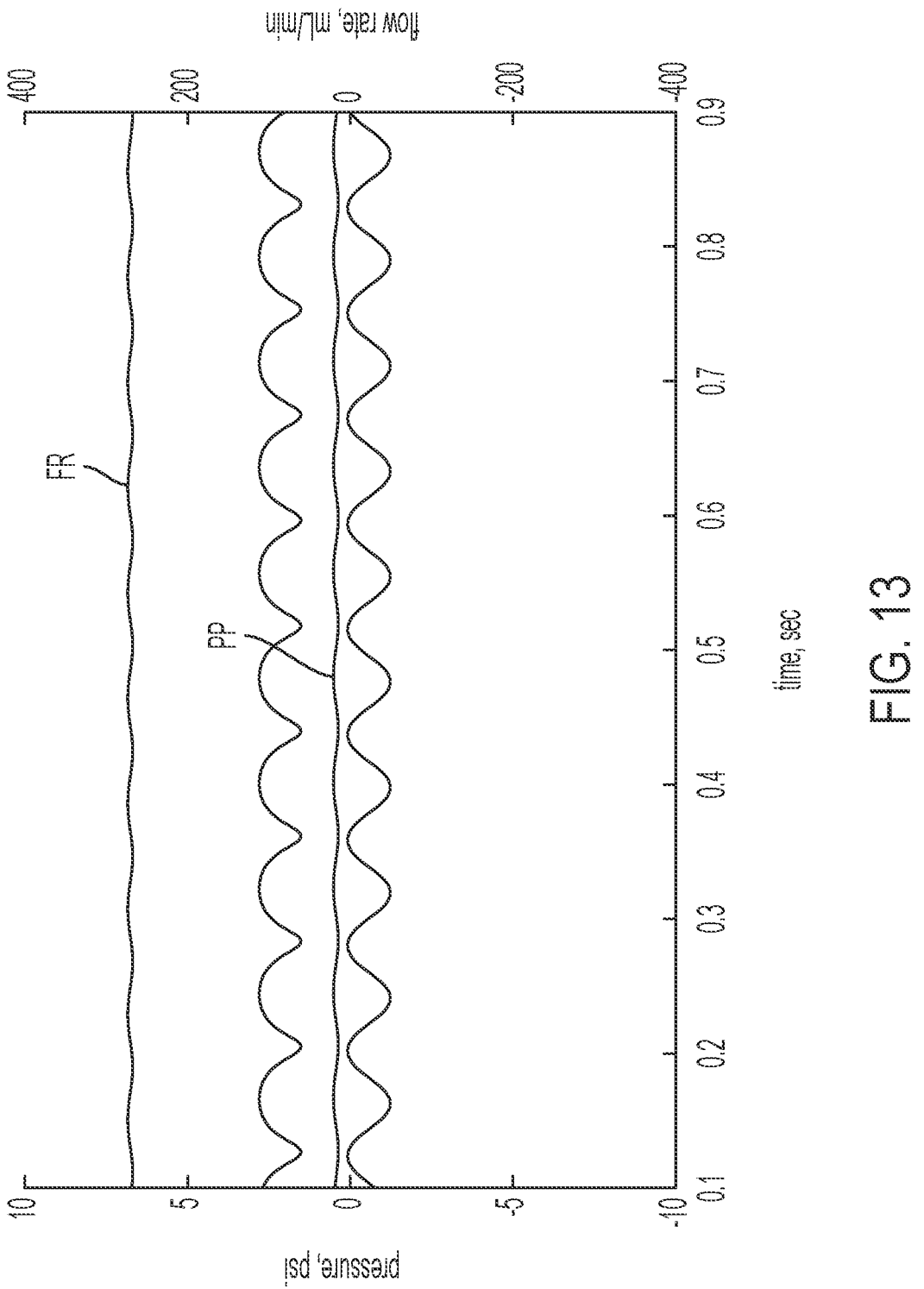
FIG. 13 is a graph illustrating a positive pressure filling output according to the peristaltic APD cycler and associated system of the present disclosure.

FIG. 13 is a graph illustrating a positive pressure patient filling output according to any of peristaltic APD cyclers 20a to 20f operating with a disposable set 100 having pressure sensing pods 112a and 112b. Pressure sensing pods 112a and 112b and associated system 10 of the present disclosure sense pressure and output signals as feedback to control unit 50, which uses the feedback as part of an algorithm, e.g., a proportional, integral and derivative ("PID") algorithm, to control the current to peristaltic pump actuator 30 so as to achieve a commanded pressure. Viewing FIGS. 2 and 3 it should be appreciated that pressure sensing pod 112b may be the pod associated with detecting positive and negative patient pumping pressure. Pressure sensing pod 112a may be used for example to ensure that a higher system pressure limit, e.g., for pumping to fresh dialysis fluid/heating container or bag 132, is not exceeded. Pressure sending pods 112a and 112b are also used by control unit 50 to detect partial or complete occlusion of any of the fluid lines 120 to 128.

Pressure sensing pods 112a and 112b also provide an enlarged dialysis fluid volume bounded on one side by flexible membrane 116, which dampens pressure pulses inherent with the actuation of peristaltic pump actuator 30. The dampening of pressure spikes is important to reduce pulsatility and increase accuracy along with maintaining the dampened pressure output at or below a safe or comfortable patient limit. FIG. 13 illustrates that at a fill flowrate FR, e.g., using sensor 80 of FIG. 12, of about 280 m/min (which is typically more than adequate), pressure sensing pods 112a and 112b enable a rather consistent positive patient pressure output PP below one psig to be simulated or determined, which is typically within a safe and comfortable range for patient P. In FIG. 13, the positive pressure PP line representing the pressure at the patient is measured in a test rig. The other two sinusoidal pressure lines in FIG. 13 are from pressure sensing pods 112a and 112b, one on the negative pressure inlet side of pump actuator 30 and the other on the positive pressure outlet side of the pump actuator. A pressure drop occurs between the positive pressure outlet side of pump actuator 30 and the patient, which is predictable, and thus the outputs from pressure sensing pods 112a and 112b set a pressure band within which an accurate positive patient pressure may be calculated or determined at control unit 50. FIG. 13 illustrates that at the very realistic flow of 280 mL/min or greater, the positive pressure PP at the patient is well within limit.

Figure 14:
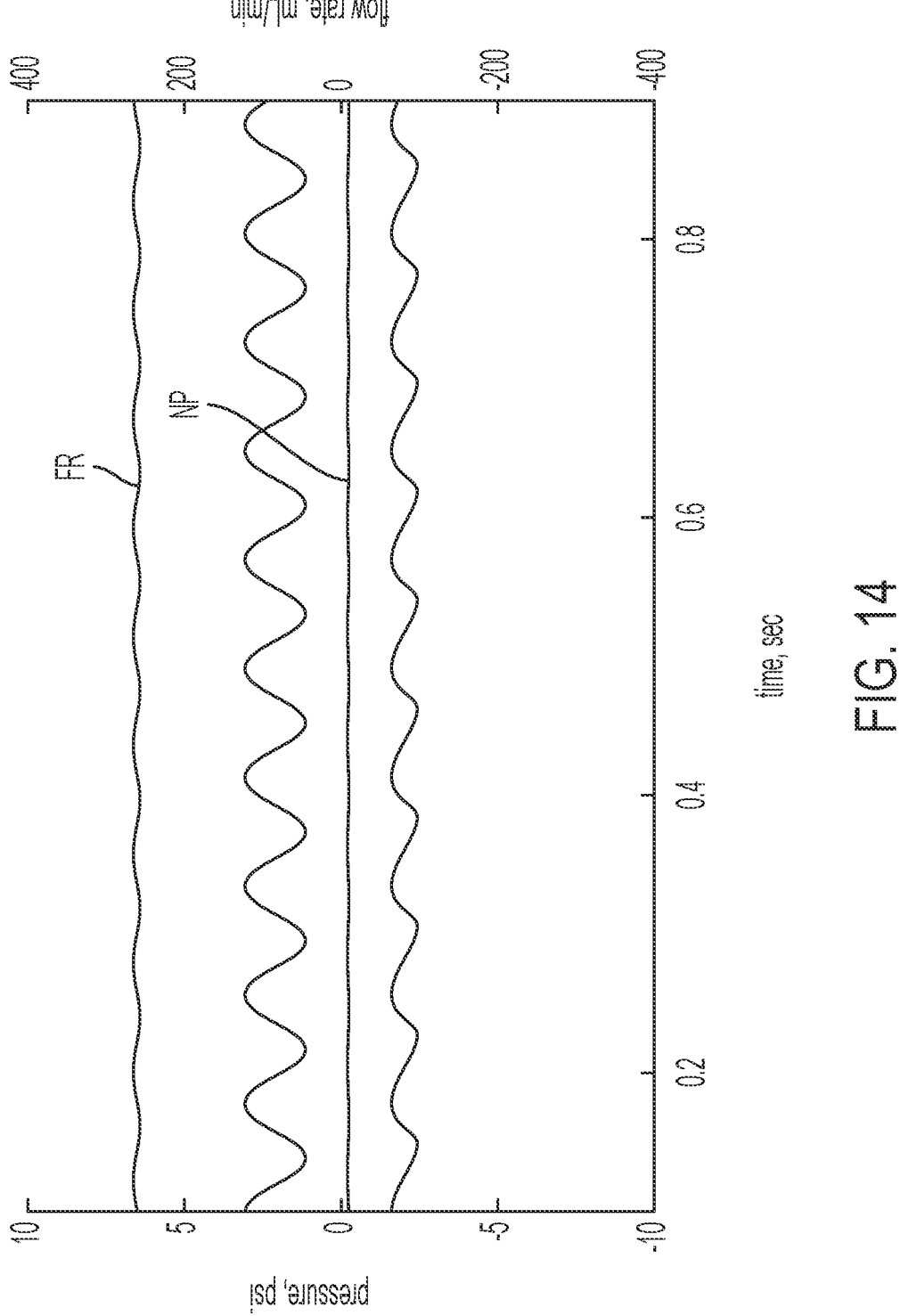
FIG. 14 is a graph illustrating a negative pressure draining output according to the peristaltic APD cycler and associated system of the present disclosure.

FIG. 14 is a graph illustrating a negative pressure patient drain output according to any of peristaltic APD cyclers 20a to 20f operating with a disposable set having pressure sensing pods 112a and 112b. FIG. 14 illustrates that at a drain flowrate FR, e.g., using sensor 80 of FIG. 12, of about 260 mL/min (which is likewise more than adequate), pressure sensing pods 112a and 112b yield a rather consistent negative patient pressure output NP less than −1 psig, which is also typically within a safe and comfortable range for patient P. Like with FIG. 13, in FIG. 14, the negative pressure NP line representing the pressure at the patient is measured in a test rig. The other two sinusoidal pressure lines in FIG. 13 are from pressure sensing pods 112a and 112b, one on the negative pressure inlet side of pump actuator 30 and the other on the positive pressure outlet side of the pump actuator. A pressure drop occurs between the negative pressure inlet side of pump actuator 30 and the patient, which is predictable, and thus the outputs from pressure sensing pods 112a and 112b set a pressure band within which an accurate negative patient pressure may be calculated or determined at control unit 50. FIG. 14 illustrates that at the very realistic flow of 260 mL/min or greater, the negative pressure PP at the patient is well within limit.

FIGS. 13 and 14 illustrate that system 10 performs well at higher flowrates needed to fill and drain the patient efficiently. It is also expected that typical APD treatments using system 10 may enter a slow flow condition, for example, during drain due to increased resistance induced in the patient's indwelling catheter caused by the catheter position inside the patient's peritoneal cavity and/or the catheter pores being partially blocked. The flowrate shown above in patient drain FIG. 14 may, for example, drop below 50 mL/min during slow flow and under the increased flow resistance. System 10 is nevertheless able to maintain accuracy and symmetry (fill versus drain accuracy) when there is no high resistance from patient catheter, e.g., over a range of flowrates, for example from 100 mL/min to greater 280 mL/min for patient filling and 15 mL/min to greater than 220 mL/min for patient draining and slow flow conditions. Thus, where it matters, when flowrates are higher, system 10 demonstrates more than sufficient accuracy.

System 10 accordingly by design commands a flowrate with speed and volume based on revolutions per minute ("RPM") and by design expects pump actuator 30 to be accurate. Pressure pods 112a and 112b indicate if system 10 is experiencing a partial or full occlusion or a slow flow condition. If so, control unit 50 employs an algorithm to either lower the flowrate (RPM) to a predefined at least one level (e.g., one or two levels) and if the problem persists as determined by the algorithm, stops pump actuator 30 and alarms at user interface 58 to alert the patient to clear the occlusion or determine an empty condition. A goal of system 10 is however to transition from drain to fill without waking the patient, so that the algorithm may be programmed such that if the low flow condition occurs after a sufficient amount of effluent has been removed from the patient, then system 10 automatically transitions to a next patient fill unless treatment is completed at the end of the drain.

Control unit 50 of cyclers 20a to 20f of system 10 is in one embodiment configured to monitor the output pressure sensing pods 112b during a patient drain to look for a patient empty detection using a pressure monitoring algorithm. Control unit 50 is programmed to look for a characteristic increase in negative pressure drop (negative suction pressure increases) in patient line 124 at the end of a patient drain as measured by pressure sensing pod 112b, wherein the characteristic increase in negative pressure at the end of drain (e.g., after a certain or threshold volume of effluent has been drained from patient P) indicates a patient empty condition. At that point, control unit 50 stops peristaltic pump actuator 30 from rotating in a draining direction (e.g., clockwise in FIGS. 2 and 3) and switches the valves from a patient drain setting to a patient fill setting (see Table 1). Control unit 50 prior to halting the patient drain may attempt a pushback of effluent in patient line 124 to see if perhaps a blockage can be cleared, allowing further draining to occur. The pushback may be provided, for example, when control unit 50, which counts peristaltic pump strokes and knows an average volume of fresh or used dialysis fluid moved per stroke, calculates that the drain volume is relatively low when the systematic decay in suction pressure is detected.

Figures 15, 16, 17:
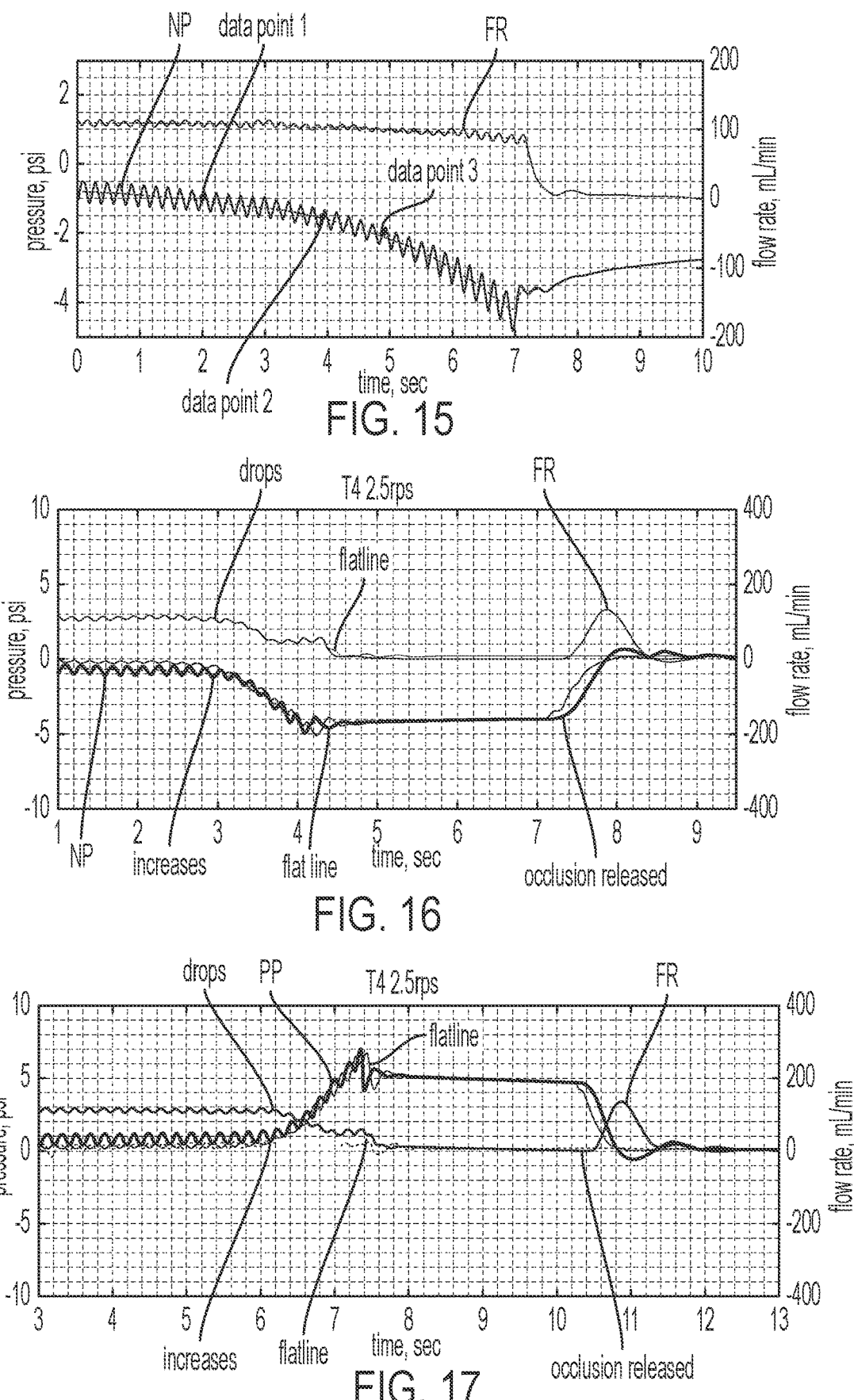
FIG. 15 is a graph illustrating a patient empty condition as detected by the peristaltic APD cycler and associated system of the present disclosure.
FIG. 16 is a graph illustrating a patient drain occlusion detection and correction performed by the peristaltic APD system of the present disclosure.
FIG. 17 is a graph illustrating a patient fill occlusion detection and correction as performed by the peristaltic APD system of the present disclosure.

FIG. 15 illustrates a patient empty detection graph using any of cyclers 20a to 20f of system 10. The upper line shows a drain flowrate FR, e.g., using sensor 80 of FIG. 12, while the lower line shows a negative pressure output NP using pressure sensing pods 112a and 112b. FIG. 15 also illustrates three example points along negative pressure output NP line, which are inputted into an algorithm used by control unit 50 to determine a patient empty condition. The first point occurs when control unit 50 determines that negative pressure output NP starts to increase or become more negative, e.g., after a certain number of readings all trend towards increased negative pressure. The second point occurs when control unit 50 determines that the negative pressure output NP increases or become more negative by a first delta amount from the first point, e.g., by −0.5 psig. The third point occurs when control unit 50 determines that negative pressure output NP increases or become more negative by a second delta amount from the first point, e.g., by −1.0 psig. Upon detecting the third point, control unit 50 in an example determines an end of drain condition and proceeds as described above. The output from flow sensor 80 may be used alternatively or additionally in an algorithm at control unit 50 to determine an end of drain, however, it is not expected that such a flow sensor is needed.

Control unit 50 of cyclers 20a to 20f of system 10 may also be programmed to detect a patient line occlusion based on a positive pressure rise (during filling) or a negative pressure rise (during draining) algorithm. A characteristic rise in suction pressure in patient line 124 measured by pressure sensing pod 112b during a patient drain indicates an occlusion to control unit 50, while a characteristic rise in positive pressure in patient line 124 measured by pressure sensing pod 112b during a patient fill indicates an occlusion to control unit 50. One or more fluid pushback attempt within patient line 124 may again be employed as part of the occlusion algorithms in an attempt to clear the occlusion and allow treatment to continue prior to alarming the patient.

FIG. 16 illustrates a full occlusion occurring during a patient drain using any of cyclers 20a to 20f of system 10. The upper line shows a drain flowrate FR, e.g., using sensor 80 of FIG. 12, while the lower line shows a negative pressure output NP using pressure sensing pods 112a and 112b. At about three seconds, drain flowrate FR drops and negative pressure output NP increases due to a large occlusion. At about 4.4 seconds, control unit 50 using the occlusion detection algorithm of the present disclosure causes pump actuator 30 to stop and the drain flowrate FR to flatline to zero, while negative pressure output NP also flatlines to a high negative pressure, indicating a full occlusion. Here, pump actuator 30 stops based on the NP increase (and/or rate of change of NP increase) occurring at about three seconds. Once pump actuator 30 stops, if NP flatlines as is the case at about 4.4 seconds, the occlusion detection algorithm determines a full occlusion and causes user interface 58 to alarm. If instead the pressure changes to static pressure, the occlusion detection algorithm instead determines a partial occlusion. At about 7.4 seconds, the occlusion is released, e.g., via a fluid pushback, and drain flowrate FR increases, while negative pressure output NP decreases to a normal patient drain level. In one example, when the occlusion is released there is a momentary surge in flowrate due to a pressure differential between the two sides of the occlusion, the patient or bag side and the pump side (pump side pressure is lower). If a pushback is employed under complete occlusion, either the occlusion will release or the pressure will rise in the opposite direction as in the case of a fill occlusion. It is contemplated for control unit 50 to look for the occlusion change in one or both of pressure and flowrate as shown here at three and 4.4 seconds, and to attempt a pushback to clear the occlusion as shown here at 7.4 seconds. The same algorithm may be employed to look for and correct a partial patient drain occlusion.

FIG. 17 illustrates a full occlusion occurring during a patient fill using any of cyclers 20a to 20f of system 10. The upper line shows a fill flowrate FR, e.g., using sensor 80 of FIG. 12, while the lower line shows a positive pressure output PP using pressure sensing pods 112a and 112b. At about 6.2 seconds, fill flowrate FR drops and positive pressure output PP increases due to a large occlusion. At about 7.6 seconds, control unit 50 using the occlusion detection algorithm of the present disclosure causes pump actuator 30 to stop and the fill flowrate FR to flatline to zero, while positive pressure output PP also flatlines to a high positive pressure, indicating a full occlusion. At about 10.4 seconds, the occlusion is released, e.g., via a fluid pushback, and drain flowrate FR increases, while positive pressure output PP decreases to a normal patient fill level. In one example, when the occlusion is released a momentary surge in flowrate occurs due to a pressure gradient between two sides of the occlusion, the pump outlet side and the patient side. It is contemplated for control unit 50 to look for the occlusion change in one or both of pressure and flowrate as shown here at 6.2 and 7.6 seconds, and to attempt a pushback to clear the occlusion as shown here at 10.4 seconds. The same algorithm may be employed to look for and correct a partial patient fill occlusion. The occlusion can either be released via a pushback from the cycler or be performed manually.

It should be understood that various changes and modifications to the presently preferred embodiments described herein will be apparent to those skilled in the art. It is therefore intended that such changes and modifications be covered by the appended claims. For example, while system 10 may count peristaltic pump strokes and multiply the count by a known volume per stroke to calculate an overall volume of fresh ore used dialysis fluid pumped to or from a patient, system 10 may alternatively or additionally provide other volume monitoring and control techniques. Moreover, as discussed above, the integration of the output of an invasive or noninvasive flow sensor to control unit 50 may be used to determine an overall volume of fresh and used dialysis fluid pumped (and thus ultrafiltration ("UF") removed from patient P). In another example, a weigh scale provided with heater 34 and a drain container (or separate fresh and used weigh scales), which outputs to control unit 50 is used to sense a weight loss associated with fresh dialysis fluid delivered to patient P and a weight gain associated with used dialysis fluid removed from patient P. Also, while inline heating is discussed in FIG. 6 being used with multiway or stopcock valves 212a to 212d, inline heating may be used instead with pinch valves.

The invention is claimed as follows:

1. A peritoneal dialysis system comprising:
   a disposable set including
      a pressure sensing manifold including first and second pressure sensing pods,
      a drain line and a dialysis fluid/heater container line in fluid communication with the first pressure sensing pod, and
      at least one additional dialysis fluid container line and a patient line in fluid communication with the second pressure sensing pod;
   a cycler including:
      a peristaltic pump actuator,
      a first valve actuator configured to operate with the first pressure sensing pod to allow dialysis fluid to selectively flow to either the drain line or the dialysis fluid/heater container line, and
      a second valve actuator configured to operate with the second pressure sensing pod to allow dialysis fluid to selectively flow to either the patient line or one of the at least one additional dialysis fluid container line; and
   a control unit programmed to operate the peristaltic pump actuator (i) in a first direction to pump fresh dialysis fluid along the at least one additional dialysis fluid container line into the dialysis fluid/heater container line, and (ii) in a reverse, second direction to pump heated, fresh dialysis fluid along the dialysis fluid/heater container line into the patient line.

2. The peritoneal dialysis system of claim 1, further comprising a peristaltic pumping tube in fluid communication with the first and second pressure sensing pods.

3. The peritoneal dialysis system of claim 1, wherein at least one of the drain line or the dialysis fluid/heater container line is connected to a port extending from the first pressure sensing pod.

4. The peritoneal dialysis system of claim 1, wherein at least one of the at least one additional dialysis fluid container line or the patient line is connected to a port extending from the second pressure sensing pod.

5. The peritoneal dialysis system of claim 1, wherein the control unit is configured to use an output from the first pressure sensing pod as feedback to control pumping in the first direction at or below a positive system pressure limit for moving the fresh dialysis fluid to a dialysis fluid/heater container.

6. The peritoneal dialysis system of claim 1, wherein the control unit is configured to use an output from the second pressure sensing pod as feedback to control pumping in the first direction at or below a negative system pressure limit for moving the fresh dialysis fluid to a dialysis fluid/heater container.

7. The peritoneal dialysis system of claim 1, wherein the control unit is configured to use an output from the second pressure sensing pod as feedback to control pumping in the second direction at or below a positive patient pressure limit for moving the fresh dialysis fluid to a patient.

8. The peritoneal dialysis system of claim 1, wherein the control unit is configured to use an output from the second pressure sensing pod as feedback to control pumping in the first direction at or below a negative patient pressure limit for removing used dialysis fluid from a patient.

9. The peritoneal dialysis system of claim 1, wherein
   the first valve actuator includes a drain valve configured to operate with the drain line and a dialysis fluid/heater valve configured to operate with the dialysis fluid/heater container line, and
   the second valve actuator includes at least one additional dialysis fluid container valve configured to operate with the at least one additional dialysis fluid container line and a patient valve configured to operate with the patient line.

10. The peritoneal dialysis system of claim 1, wherein the cycler further includes a heater under control of the control unit for heating the fresh dialysis fluid delivered to a first dialysis fluid/heater container via the dialysis fluid/heater container line.

11. The peritoneal dialysis system of claim 1, wherein at least one of the first and second pressure sensing pods includes a flexible diaphragm that transmits fresh and used dialysis fluid pressure fluctuations to a pressure transmission fluid.

12. The peritoneal dialysis system of claim 11, wherein the flexible diaphragm is further configured to dampen pressure fluctuations.

13. The peritoneal dialysis system of claim 1, wherein the control unit is further configured to end a patient drain when a negative pressure increase is sensed by the second pressure sensing pod while the peristaltic pump actuator is operated in the first direction to pump used dialysis fluid from the patient line.

14. The peritoneal dialysis system of claim 13, wherein the control unit is configured to end the patient drain when the negative pressure increase is sensed and the control unit has determined that at least a threshold amount of the used dialysis fluid has been removed from a patient.

15. The peritoneal dialysis system of claim 13, wherein the control unit is configured to end the patient drain when the negative pressure increase is sensed and after a pushback of the used dialysis fluid in the patient line by the peristaltic pump actuator operating in the second direction fails to remove the negative pressure increase.

16. The peritoneal dialysis system of claim 1, wherein the control unit is further configured to determine that a patient line occlusion has occurred when the second pressure sensing pod senses an increase in positive pressure in the patient line while moving the fresh dialysis fluid to a patient.

17. The peritoneal dialysis system of claim 1, wherein the control unit is further configured to determine that a patient line occlusion has occurred when the second pressure sensing pod senses an increase in negative pressure in the patient line while removing used dialysis fluid from a patient.

18. The peritoneal dialysis system of claim 1, wherein the control unit is further configured to perform a patient fill according to a fill profile in which a speed of the peristaltic pump actuator operating in the second direction is increased for a middle portion of the patient fill.

19. The peritoneal dialysis system of claim 1, wherein the control unit is further configured to perform a patient drain according to a drain profile in which a speed of the peristaltic pump actuator operating in the first direction is increased for a middle portion of the patient drain.

20. The peritoneal dialysis system of claim 1, wherein the peristaltic pump actuator is positioned relative to the cycler such that the first and second pressure sensing pods, the drain line, the dialysis fluid/heater container line, the at least one additional dialysis fluid container line, and the patient line are oriented at least substantially horizontally for treatment.

21. The peritoneal dialysis system of claim 20, wherein the peristaltic pump actuator is located on a tray that slides into and out of the cycler.

22. The peritoneal dialysis system of claim 20, wherein the peristaltic pump actuator is accessible from a top of the cycler.

23. The peritoneal dialysis system of claim 1, wherein the peristaltic pump actuator is positioned relative to the cycler such that the first and second pressure sensing pods, the drain line, the dialysis fluid/heater container line, the at least one additional dialysis fluid container line, and the patient line are oriented at least substantially vertically for treatment.

24. The peritoneal dialysis system of claim 23, wherein the cycler further includes a plurality of valves, a first door configured to selectively cover the plurality of valves, and a second door configured to selectively cover the peristaltic pump actuator.

25. The peritoneal dialysis system of claim 1, wherein the first and second pressure sensing pods are spaced at least one of (i) symmetrically about, or (ii) equidistant to the peristaltic pump actuator.

* * * * *